US012053315B2

(12) United States Patent
Tajima et al.

(10) Patent No.: US 12,053,315 B2
(45) Date of Patent: Aug. 6, 2024

(54) MEDICAL IMAGE CAPTURING APPARATUS, METHOD FOR OPERATING MEDICAL IMAGE CAPTURING APPARATUS, AND OPERATION PROGRAM FOR MEDICAL IMAGE CAPTURING APPARATUS

(71) Applicant: FUJIFILM CORPORATION, Tokyo (JP)

(72) Inventors: Takashi Tajima, Kanagawa (JP); Munetaka Kato, Kanagawa (JP); Masakazu Fukuyo, Kanagawa (JP); Takeyasu Kobayashi, Kanagawa (JP); Hisatsugu Horiuchi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 282 days.

(21) Appl. No.: 17/720,246

(22) Filed: Apr. 13, 2022

(65) Prior Publication Data
US 2022/0346743 A1 Nov. 3, 2022

(30) Foreign Application Priority Data

Apr. 28, 2021 (JP) .................................. 2021-076587

(51) Int. Cl.
*A61B 6/00* (2024.01)
*A61B 6/03* (2006.01)
*A61B 6/40* (2024.01)

(52) U.S. Cl.
CPC ............ *A61B 6/4435* (2013.01); *A61B 6/032* (2013.01); *A61B 6/035* (2013.01); *A61B 6/488* (2013.01);

(Continued)

(58) Field of Classification Search
CPC .............................. A61B 6/4435; A61B 6/035
See application file for complete search history.

(56) References Cited

U.S. PATENT DOCUMENTS

| 5,042,487 A * | 8/1991 | Marquardt ........... A61B 6/0478 |
| | | 5/618 |
| 6,735,274 B1 * | 5/2004 | Zahavi ................. A61B 6/4028 |
| | | 378/4 |

(Continued)

FOREIGN PATENT DOCUMENTS

JP 2017-077464 A 4/2017

*Primary Examiner* — Chih-Cheng Kao
(74) *Attorney, Agent, or Firm* — SOLARIS Intellectual Property Group, PLLC

(57) ABSTRACT

A CT apparatus includes an annular frame that rotates around a subject positioned in a bore, three columns that hold the frame to be rotatable and movable up and down in a vertical, an elevation mechanism that moves up and down the frame, and a rotation mechanism that rotates the frame. A radiation source and a radiation detector are attached to the frame at positions facing each other. The frame has a width smaller than a width of the radiation source and the radiation detector in a height direction over a whole periphery. An imaging controller performs control for operating the elevation mechanism in response to a return instruction from an operator to move the frame to a retreat height position set at a position of a highest point in an elevation range of the frame on an upper end side of the columns. The imaging controller performs control for operating the rotation mechanism in response to the return instruction from the operator to rotate the frame to a position of 60° that is a first rotation position where the radiation source overlaps the columns.

13 Claims, 30 Drawing Sheets

(52) U.S. Cl.
CPC .......... *A61B 6/4064* (2013.01); *A61B 6/4405* (2013.01); *A61B 6/545* (2013.01)

(56) References Cited

U.S. PATENT DOCUMENTS

| | | | |
|---|---|---|---|
| 2008/0292053 A1* | 11/2008 | Marash | A61B 6/04 378/65 |
| 2009/0116617 A1* | 5/2009 | Mastronardi | G01V 5/222 378/57 |
| 2017/0105691 A1 | 4/2017 | Shindo et al. | |

\* cited by examiner

FIG. 10

IRRADIATION CONDITION TABLE — 71

| IMAGING PROCEDURE | IRRADIATION CONDITION (TUBE VOLTAGE TUBE CURRENT IRRADIATION TIME) | SCOUT IMAGING POSITION | | | 
|---|---|---|---|---|
| | | REFERENCE HEIGHT POSITION | SECOND AND THIRD ROTATION POSITIONS | FOURTH ROTATION POSITION (ROTATION START POSITION) |
| UPRIGHT HEAD ADULT MALE | 100 kV 10 mA 0.5 ms | 170 cm | 0° | 0° |
| UPRIGHT HEAD ADULT FEMALE | 100 kV 10 mA 0.5 ms | 155 cm | 0° | 0° |
| UPRIGHT NECK ADULT MALE | 80 kV 8 mA 0.5 ms | 160 cm | 0° | 0° |
| ... | | | | |
| SITTING SPINE ADULT MALE | 120 kV 12 mA 0.5 ms | 80 cm | 0°, 90° | 90° |
| SITTING SPINE ADULT FEMALE | 120 kV 12 mA 0.5 ms | 70 cm | 0°, 90° | 90° |
| ... | | | | |

86

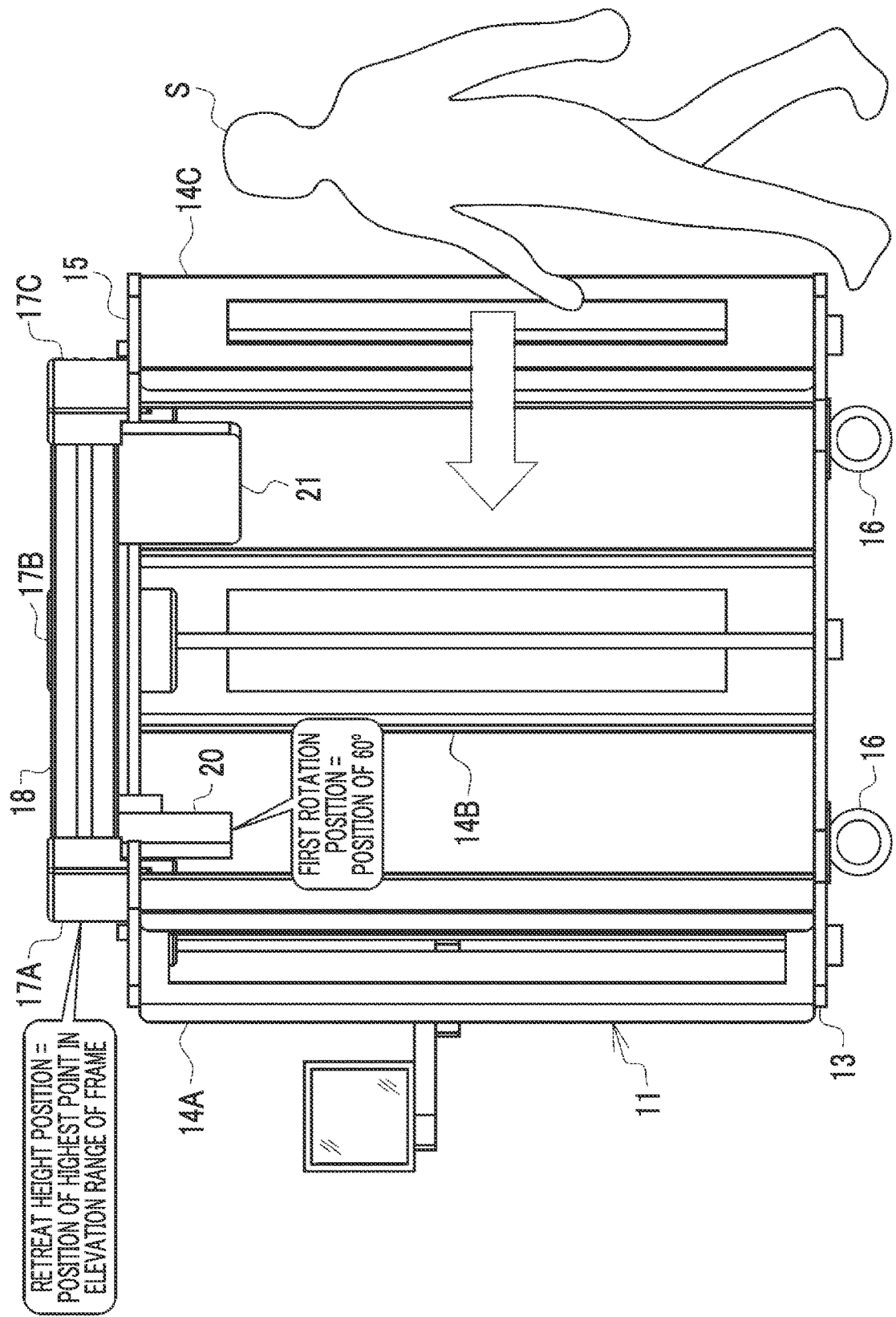

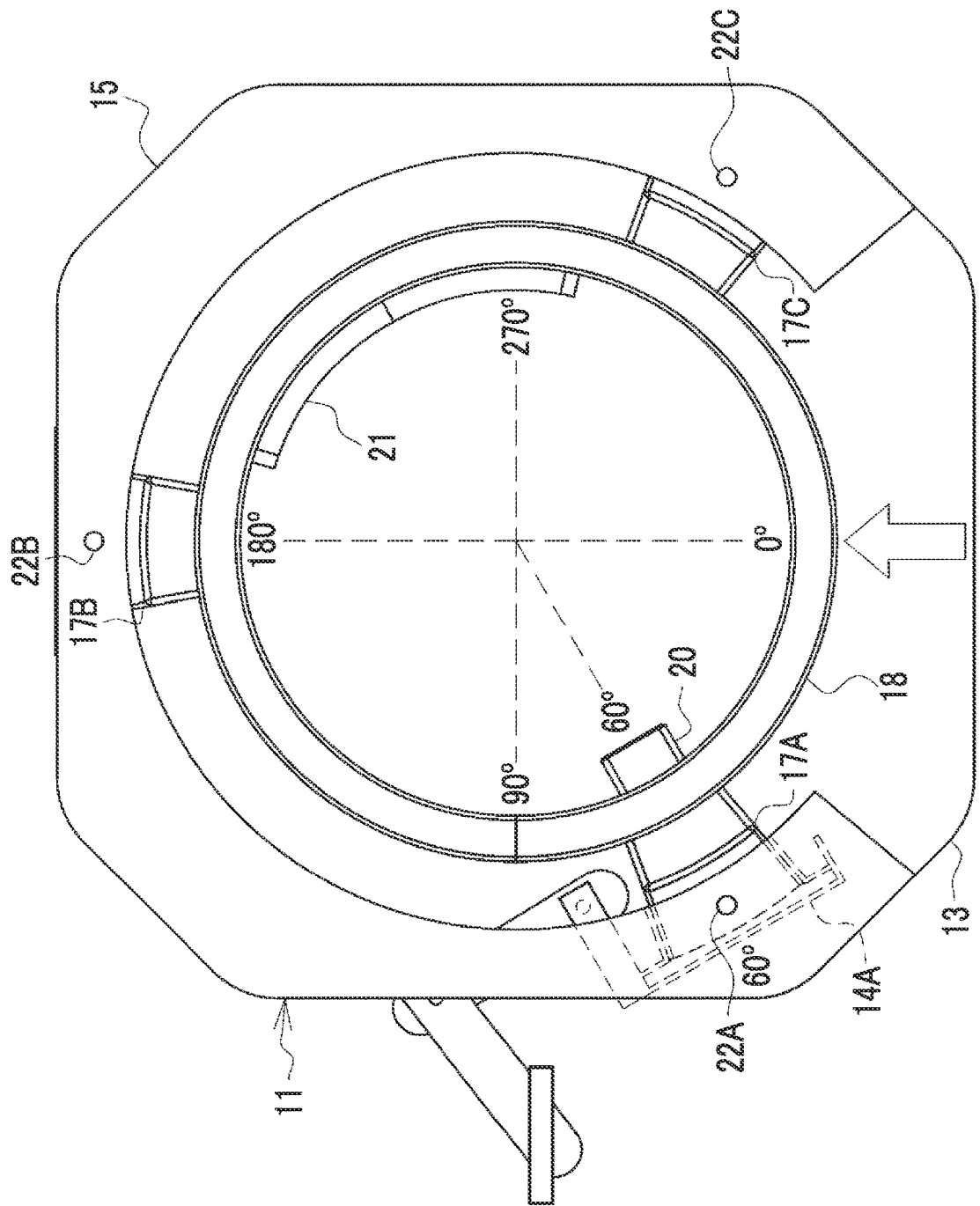

MEDICAL IMAGE CAPTURING APPARATUS, METHOD FOR OPERATING MEDICAL IMAGE CAPTURING APPARATUS, AND OPERATION PROGRAM FOR MEDICAL IMAGE CAPTURING APPARATUS

CROSS-REFERENCE TO RELATED APPLICATIONS

The present application claims priority under 35 U.S.C. § 119 to Japanese Patent Application No., 2021-076587 filed on Apr. 28, 2021. The above application is hereby expressly incorporated by reference, in its entirety, into the present application.

BACKGROUND

1. Technical Field

A technique of the present disclosure relates to a medical image capturing apparatus, an operation method of a medical image capturing apparatus, and an operation program for a medical image capturing apparatus.

2. Description of the Related Art

For example, a medical image capturing apparatus, such as a computed tomography (CT) apparatus for imaging a subject in an upright posture described in JP2017-077464A, has been suggested. The CT apparatus described in JP2017-077464A comprises an imaging unit, and two columns that hold the imaging unit. The imaging unit is in an annular shape, and the subject in the upright posture is positioned in a bore. The two columns are disposed in a front-rear direction of the subject. The columns can expand and contract, and accordingly, a height position of the imaging unit can be changed.

The imaging unit is configured of a radiation source that emits radiation, a radiation detector that detects radiation, a frame, and an annular cover that accommodates the radiation source, the radiation detector, and the frame. The cover has a width greater than a width of the radiation source and the radiation detector in a height direction over a whole periphery. The radiation source and the radiation detector are attached to the frame. The subject is irradiated with radiation from the radiation source at each predetermined angle while rotating the frame, and radiation transmitted through the subject is detected in the radiation detector, whereby a plurality of projection images are obtained. Then, a plurality of projection images are reconstructed, and a tomographic image is obtained.

SUMMARY

In the medical image capturing apparatus, such as the CT apparatus described in JP2017-077464A, as a method of making the subject approach the bore of the imaging unit, the following two ways are considered. That is, a first method is a method that the imaging unit is retreated above the head of the subject such that a lower edge of the imaging unit exceeds the head of the subject, the subject is made upright at a place corresponding to the bore, and then, the imaging unit is moved down to an imaging position. A second method is a method that moves down the imaging unit to a lowest point, disposes the subject across the imaging unit to make the subject upright at a place corresponding to the bore, and then, moves up the imaging unit to an imaging position.

Note that the cover of the imaging unit has a certain degree of width to accommodate the radiation source, the radiation detector, and the frame as described above. For this reason, the first method has a problem in that there is a need to secure a comparatively large space for retreating the imaging unit above the head of the subject in an upper portion of the apparatus. The second method has a problem in that, since the imaging unit having a certain degree of width is disposed across the subject, a burden is imposed on the subject.

An embodiment according to the technique of the present disclosure provides a medical image capturing apparatus that makes a subject easily approach inside the apparatus, an operation method of a medical image capturing apparatus, and an operation program for a medical image capturing apparatus.

A medical image capturing apparatus of the present disclosure comprises a radiation source that emits radiation, a radiation detector that detects the radiation, an annular frame to which the radiation source and the radiation detector are attached at positions facing each other and that rotates around a subject positioned in a bore, the frame having a width smaller than a width of the radiation source and the radiation detector in a height direction over a whole periphery, and both the radiation source and the radiation detector protruding from either an upper edge or a lower edge; a plurality of columns that hold the frame to be rotatable and movable up and down in a vertical direction, a moving mechanism that moves up and down and rotates the frame, a processor, and a memory connected to or embedded in the processor. The processor performs control for operating the moving mechanism to move the frame to a retreat height position set on an upper end side or a lower end side of the columns and control for operating the moving mechanism to rotate the frame to a first rotation position where at least one of at least a part of the radiation source or at least a part of the radiation detector overlaps the columns, in response to an operation instruction from an operator.

It is preferable that the radiation source and the radiation detector protrude from the lower edge, and the retreat height position is a position of a highest point in an elevation range of the frame.

It is preferable that the radiation source and the radiation detector protrude from the upper edge, and the retreat height position is a position of a lowest point in an elevation range of the frame.

It is preferable that the processor performs control for operating the moving mechanism to move the frame to a scout imaging position where scout imaging is performed before main imaging and that is at least one of a second rotation position where the radiation source confronts the subject or a third rotation position where the radiation source faces a side surface of the subject, in response to the operation instruction from the operator.

It is preferable that the processor operates the moving mechanism to rotate the frame to a fourth rotation position, and then, causes the radiation source and the radiation detector to perform main imaging while rotating the frame to a fifth rotation position.

It is preferable that the processor operates the moving mechanism after the main imaging to return the frame from the fifth rotation position to the first rotation position.

It is preferable that the processor rotates the frame in a direction from the fifth rotation position toward the fourth rotation position in a case of returning the frame from the fifth rotation position to the first rotation position.

It is preferable that the processor rotates the frame at a rotation speed higher than a rotation speed from the fourth rotation position to the fifth rotation position in a case of returning the frame from the fifth rotation position to the first rotation position.

It is preferable that the medical image capturing apparatus further includes casters for transport.

It is preferable that the radiation source emits the radiation having a pyramidal shape.

It is preferable that the subject is positioned in the bore in any one of an upright posture or a sitting posture.

An operation method of a medical image capturing apparatus of the present disclosure is an operation method of a medical image capturing apparatus including a radiation source that emits radiation, a radiation detector that detects the radiation, an annular frame to which the radiation source and the radiation detector are attached at positions facing each other and that rotates around a subject positioned in a bore, the frame having a width smaller than a width of the radiation source and the radiation detector in a height direction over a whole periphery, and both the radiation source and the radiation detector protruding from either an upper edge or a lower edge, a plurality of columns that hold the frame to be rotatable and movable up and down in a vertical direction, and a moving mechanism that moves up and down and rotates the frame, and comprises performing control for operating the moving mechanism to move the frame to a retreat height position set on an upper end side or a lower end side of the columns and control for operating the moving mechanism to rotate the frame to a first rotation position where at least one of at least a part of the radiation source or at least a part of the radiation detector overlaps the columns, in response to an operation instruction from an operator.

An operation program for a medical image capturing apparatus of the present disclosure is an operation program for a medical image capturing apparatus including a radiation source that emits radiation, a radiation detector that detects the radiation, an annular frame to which the radiation source and the radiation detector are attached at positions facing each other and that rotates around a subject positioned in a bore, the frame having a width smaller than a width of the radiation source and the radiation detector in a height direction over a whole periphery, and both the radiation source and the radiation detector protruding from either an upper edge or a lower edge, a plurality of columns that hold the frame to be rotatable and movable up and down in a vertical direction, and a moving mechanism that moves up and down and rotates the frame, and causes a computer to execute processing including performing control for operating the moving mechanism to move the frame to a retreat height position set on an upper end side or a lower end side of the columns and control for operating the moving mechanism to rotate the frame to a first rotation position where at least one of at least a part of the radiation source or at least a part of the radiation detector overlaps the columns, in response to an operation instruction from an operator.

According to the technique of the present disclosure, it is possible to a medical image capturing apparatus that makes a subject easily approach inside the apparatus, an operation method of a medical image capturing apparatus, and an operation program for a medical image capturing apparatus.

BRIEF DESCRIPTION OF THE DRAWINGS

Exemplary embodiments according to the technique of the present disclosure will be described in detail based on the following figures, wherein:

FIG. 10 is a diagram showing an irradiation condition table;

FIG. 11 is a diagram showing a scene where the subject is led inside the apparatus body in a state in which a frame is at a retreat height position and a first rotation position;

FIG. 12 is a diagram showing a state in which the frame is rotated to the first rotation position;

DETAILED DESCRIPTION

Figure 1:
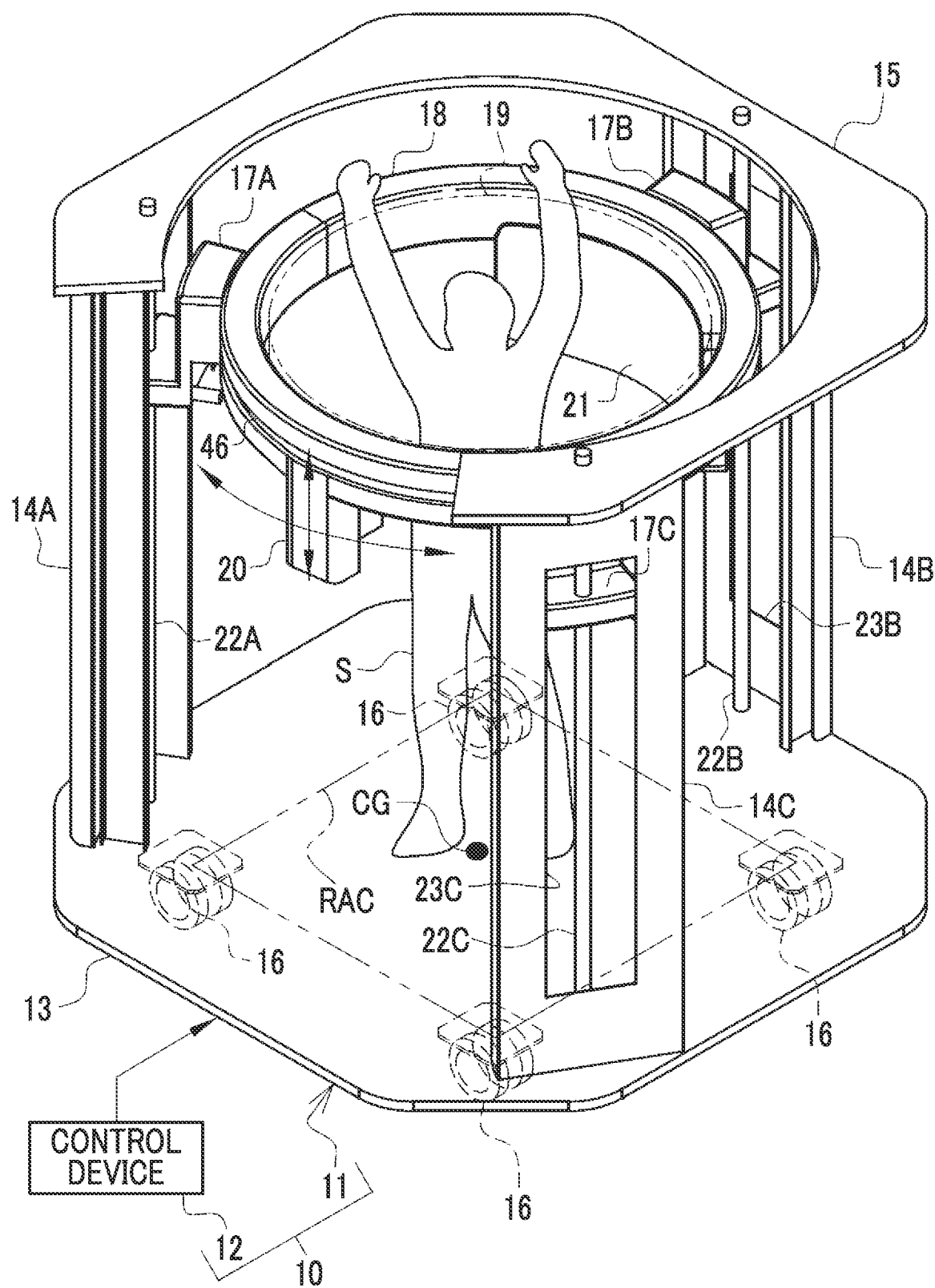
FIG. 1 is a perspective view showing a CT apparatus.

As shown in FIG. 1 as an example, a CT apparatus 10 is an apparatus that obtains a tomographic image TI (see FIG. 16) of a subject S, and is configured of an apparatus body 11 and a control device 12. The apparatus body 11 is installed, for example, in an imaging room of a medical facility. The control device 12 is installed, for example, in a control room next to the imaging room. The control device 12 is a desktop type personal computer, a notebook type personal computer, or a tablet terminal. The CT apparatus 10 is an example of a "medical image capturing apparatus" according to the technique of the present disclosure.

As shown in FIGS. 1 to 4 as an example, the apparatus body 11 comprises a stage 13, three columns 14A, 14B, and 14C, and a top plate 15. The stage 13 is a flat plate having an octagonal shape. Casters 16 for transport are attached to four corners of a back surface of the stage 13.

The casters 16 comprise a rotation locking mechanism (not shown), and after the apparatus body 11 is installed at an installation place, the rotation of the casters 16 can be locked by operating the rotation lock mechanism. Alternatively, the casters 16 can be detached from the stage 13, and after the apparatus body 11 is installed at the installation place, the casters 16 can be detached. In a case where the frame 18 and the like is viewed in plan view from above, and a quadrangle RAC (see FIG. 1) with the four casters 16 as apexes is assumed, a center of gravity CG (see FIG. 1) of the apparatus body 11 falls within the quadrangle RAC. The center of gravity CG is, for example, a center of the stage 13. For this reason, it is possible to stably transport the apparatus body 11. In a case of installing the apparatus body 11 without detaching the casters 16, the installation stability of the apparatus body 11 is increased.

The columns 14A to 14C have an appearance in a rectangular plate shape, and are provided upright at four corners of a front surface of the stage 13. The columns 14A and 14C are disposed right and left on a front surface side of the apparatus body 11 (right and left in front of the subject S). The column 14B is disposed at a center (behind the subject S) on a back surface side of the apparatus body 11. The top plate 15 is attached to upper end portions of the columns 14A to 14C. The top plate 15 has an appearance in an octagonal shape following the stage 13. The top plate 15 has a C shape in which a center portion is hollowed in a circular shape and a portion on the front surface side of the apparatus body 11 between the columns 14A and 14C is notched. In the following description, in a case where there is no need for particular distinction, the columns 14A to 14C are collectively described as the columns 14.

A connecting member 17A is connected to the column 14A, a connecting member 17B is connected to the column 14B, and a connecting member 17C is connected to the column 14C. A frame 18 is connected to the connecting members 17A to 17C. That is, the columns 14A to 14C and the frame 18 are connected through the connecting members 17A to 17C. In the following description, in a case where there is no need for particular distinction, the connecting members 17A to 17C are collectively described as the connecting members 17.

The frame 18 has an annular shape. The subject S is positioned at a position of a center C (see FIG. 4) of a bore 19 of the annular frame 18. In FIGS. 1 to 4, a scene where the subject S in an upright posture with both hands up over a head is positioned is shown.

The columns 14 are provided with guide rails (not shown) that are fitted to the connecting members 17. The connecting members 17 and the frame 18 can move up and down in a vertical direction along the guide rails. That is, the columns 14 hold the frame 18 to be movable up and down in the vertical direction. The frame 18 can rotate around the subject S with the center C as a center axis. That is, the columns 14A to 14C hold the frame 18 to be rotatable around the subject S. The columns 14 may expand and contract to change a height position of the frame 18.

A radiation source 20 that emits radiation R (see FIG. 6), such as X-rays or γ-rays, and a radiation detector 21 that detects the radiation R are attached to the frame 18. The radiation source 20 and the radiation detector 21 are disposed at positions facing each other (positions at an interval of 180°) of the frame 18. The radiation source 20 has a box shape, and the radiation detector 21 has a pad shape. In a case where the frame 18 and the like are viewed in a direction in plan view from above, the radiation detector 21 has an arc shape following the shape of the frame 18. The frame 18 has a width W1 smaller than a width (here, a width of the radiation detector 21 in a height direction greater than the radiation source 20) W2 of the radiation source 20 and the radiation detector 21 in a height direction over a whole periphery (see FIG. 2). Both the radiation source 20 and the radiation detector 21 protrude from a lower edge of the frame 18.

A screw shaft 22A is provided in the column 14A, a screw shaft 22B is provided in the column 14B, and a screw shaft 22C is provided in the column 14C. The screw shafts 22A to 22C have a height from the stage 13 to the top plate 15. The screw shafts 22A to 22C rotate, whereby the connecting members 17A to 17C and the frame 18 move up and down in the vertical direction. In the following description, in a case where there is no need for particular distinction, the screw shafts 22A to 22C are collectively described as the screw shafts 22.

The column 14A has an opening 23A, the column 14B has an opening 23B, and the column 14C has an opening 23C. The openings 23A to 23C are formed by hollowing most of the columns 14A to 14C in a rectangular shape. It is possible to visually recognize the subject S from the outside of the apparatus body 11 through the openings 23A to 23C. Since there are the openings 23A to 23C, each of the columns 14A to 14C partially looks like two parts; however, the two parts of each of the columns 14A to 14C are linked on the upper and lower sides of each of the openings 23A to 23C, and the number of parts is one. In the following description, in a case where there is no need for particular distinction, the openings 23A to 23C are collectively described as the openings 23.

A touch panel display 25 is attached to the column 14A through a movable arm 24. The touch panel display 25 is operated by an operator of the CT apparatus 10, such as a radiographer. The touch panel display 25 displays various kinds of information to the operator.

An attachment portion 26 (see FIG. 4) of the column 14A for the movable arm 24 is thicker than other portions and rigidity is increased. The attachment portion 26 is provided only in the column 14A, and is not provided in the columns 14B and 14C. For this reason, the column 14A has rigidity higher than the columns 14B and 14C.

Figure 4:
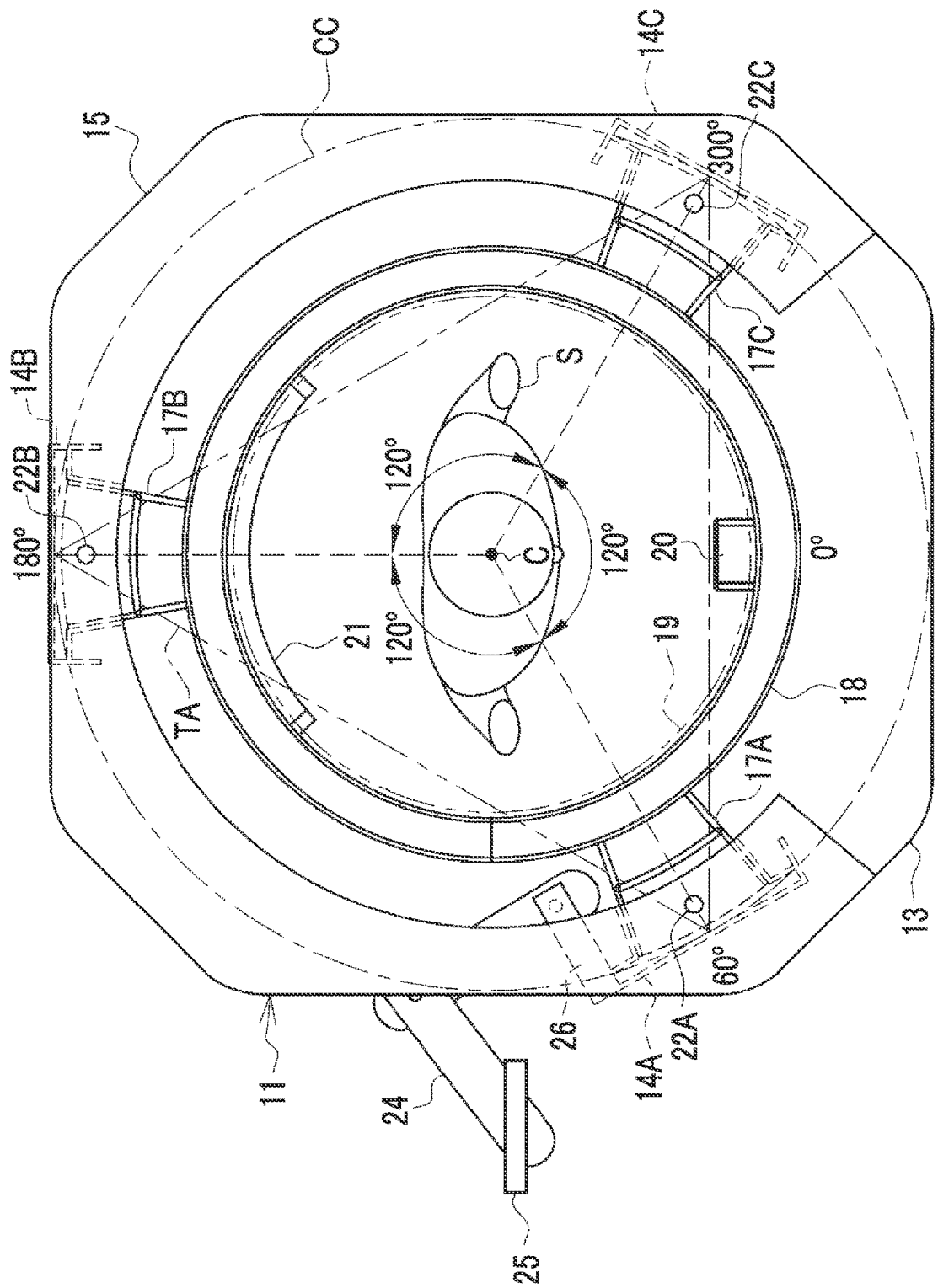
FIG. 4 is a top view of the apparatus body of the CT apparatus.

In FIG. 4 in which the frame 18 and the like are viewed in plan view from above, in a case where a position where there is the radiation source 20 on the front surface of the apparatus body 11 is referred to as a position of 0°, the column 14A is disposed at a position of 60° on a circle CC centering on the center C of the frame 18, the column 14B is disposed at a position of 180° on the circle CC, and the column 14C is disposed at a position of 300° on the circle CC. That is, the columns 14A to 14C are disposed at 120° intervals (at regular intervals on the same periphery). In a case where a triangle TA (a regular triangle inscribed in the circle CC) with the columns 14A to 14C as apexes is assumed, the center C of the frame 18 falls within the triangle TA. The angles of "0°", "60°", and the like indicate "0°", "60°", and the like in a meaning including an error that is generally allowed in the technical field to which the technique of the present disclosure belongs, and an error to such an extent not contrary to the spirit and scope of the technique of that the present disclosure, in addition to completely "0°", "60°", and the like. The "regular intervals" indicate regular intervals in a meaning including an error that is generally allowed in the technical field to which the technique of the present disclosure belongs, and an error to such an extent not contrary to the spirit and scope of the technique of that the present disclosure, in addition to completely regular intervals.

Figure 5:
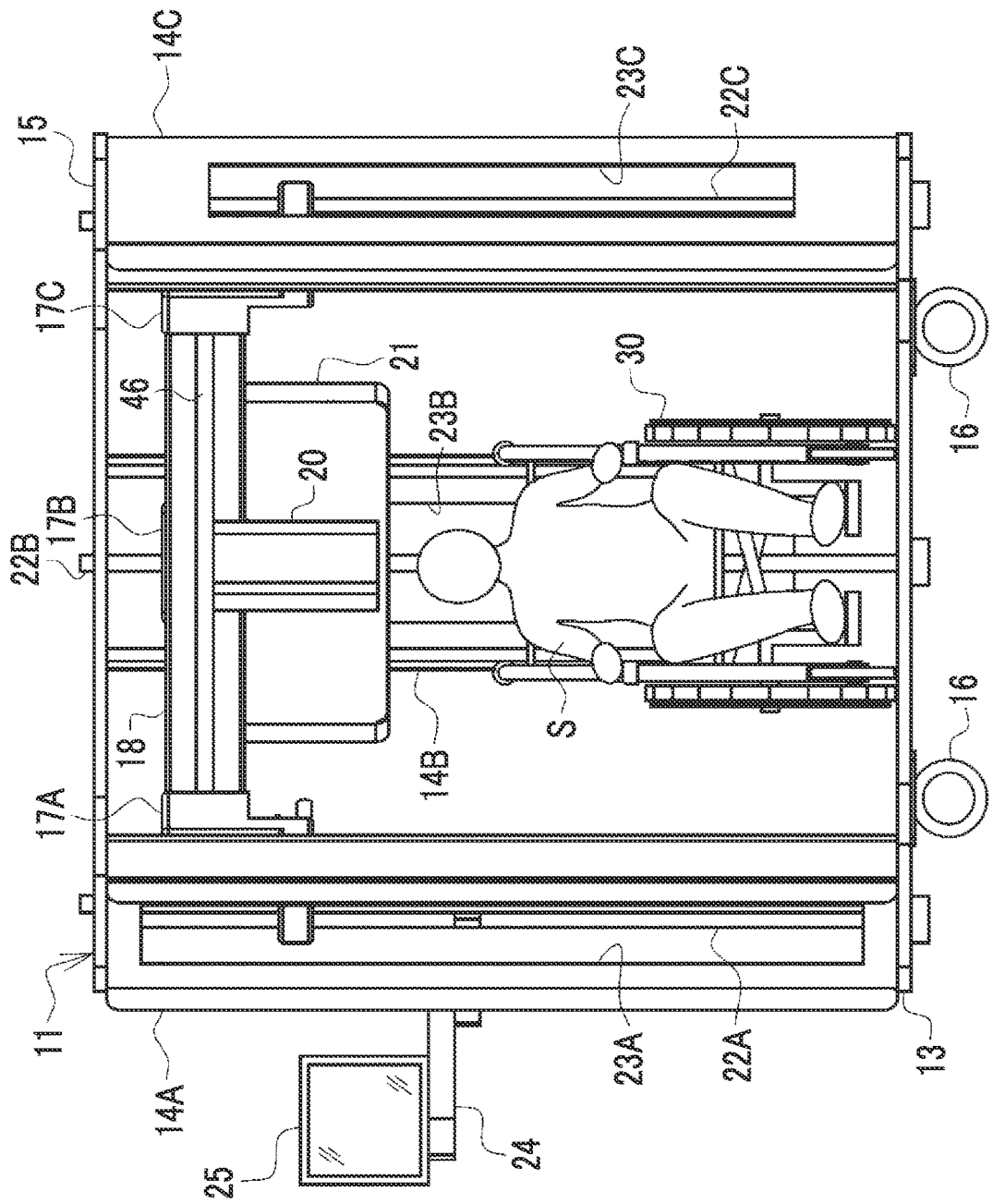
FIG. 5 is a front view of the apparatus body of the CT apparatus showing a state in which a subject in a sitting posture on a wheelchair is positioned.

In FIGS. 1 to 4, although an example where the subject S in the upright posture with both hands up over the head is positioned in the bore 19 has been shown, the technique of the present disclosure is not limited thereto. As shown in FIG. 5 as an example, the CT apparatus 10 can also position the subject S in a sitting posture on a wheelchair 30 in the bore 19 and image the subject S. Both the subject S in the upright posture and the subject S in the sitting posture on the wheelchair 30 are positioned such that a front surface thereof turns toward the position of 0°.

Figure 6:
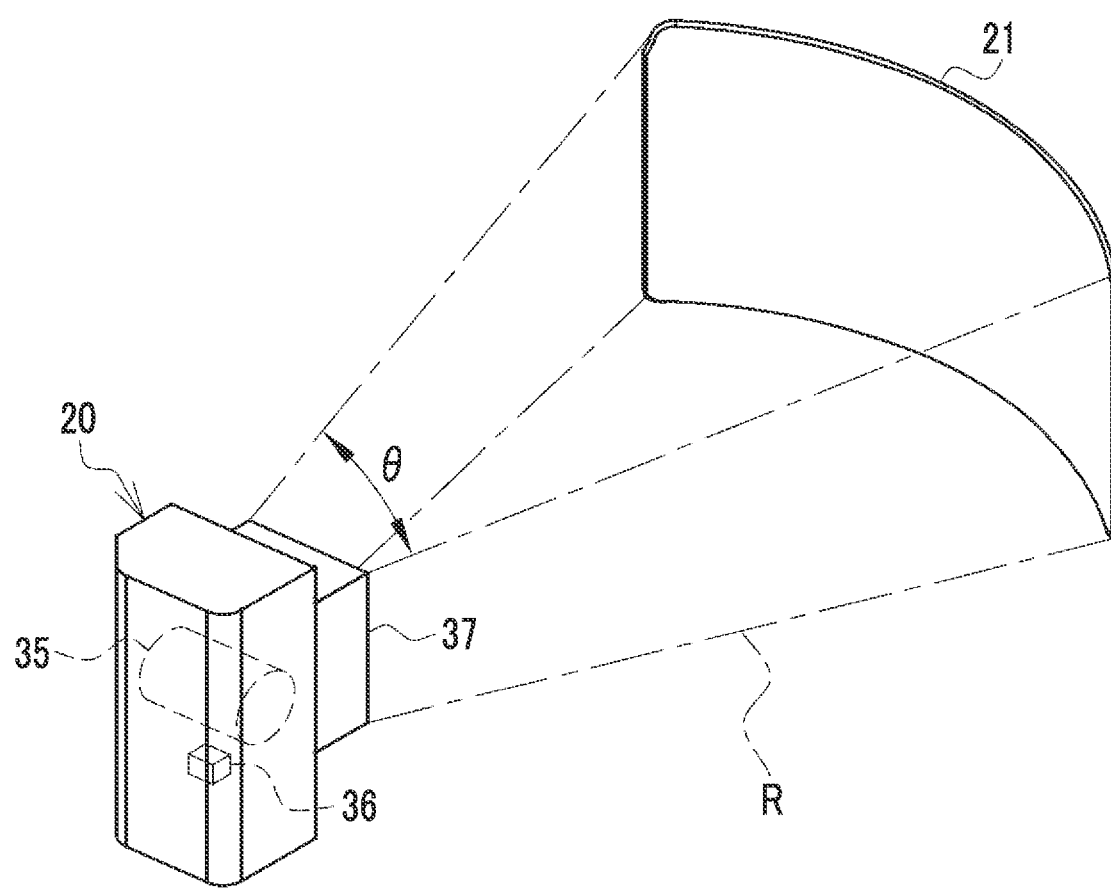
FIG. 6 is a perspective view showing a radiation source, a radiation detector, and radiation.

As shown in FIG. 6 as an example, the radiation source 20 incorporates a radiation tube 35 and an irradiation field lamp 36. The radiation tube 35 emits the radiation R. The irradiation field lamp 36 emits, for example, orange visible light indicating an irradiation field of the radiation R.

The radiation source 20 has an irradiation field limiter 37. The irradiation field limiter 37 is also referred to as a collimator and defines the irradiation field of the radiation R to the radiation detector 21. In the irradiation field limiter 37, an incidence opening into which the radiation R from the radiation tube 35 is incident, and an emission opening from which the radiation R is emitted are formed. For example, four shielding plates are provided near the emission opening. The shielding plates are formed of a material for shielding the radiation R, for example, lead. The shielding plates are disposed on sides of the quadrangles, in other words, are assembled in a double-cross shape (checkered pattern), and forms an irradiation opening of the quadrangle that transmits the radiation R. The irradiation field limiter 37 changes the size of the irradiation opening by changing positions of the shielding plates, and with this, the irradiation field of the radiation R to the radiation detector 21 is changed. With the operation of the irradiation field limiter 37, the radiation R in a quadrangular pyramidal shape is emitted from the radiation source 20. A radiation angle θ of the radiation R is, for example, 45°.

The radiation detector 21 has, for example, a scintillator that converts the radiation R into visible light, a thin film transistor (TFT) substrate on which pixels for storing electric charge depending on visible light converted from the radiation R are arranged in a two-dimensional shape, and a signal processing circuit that outputs a voltage signal depending on electric charge as a projection image. The radiation detector 21 may be of a type of directly detecting the radiation R instead of visible light converted from the radiation R.

Figure 7:
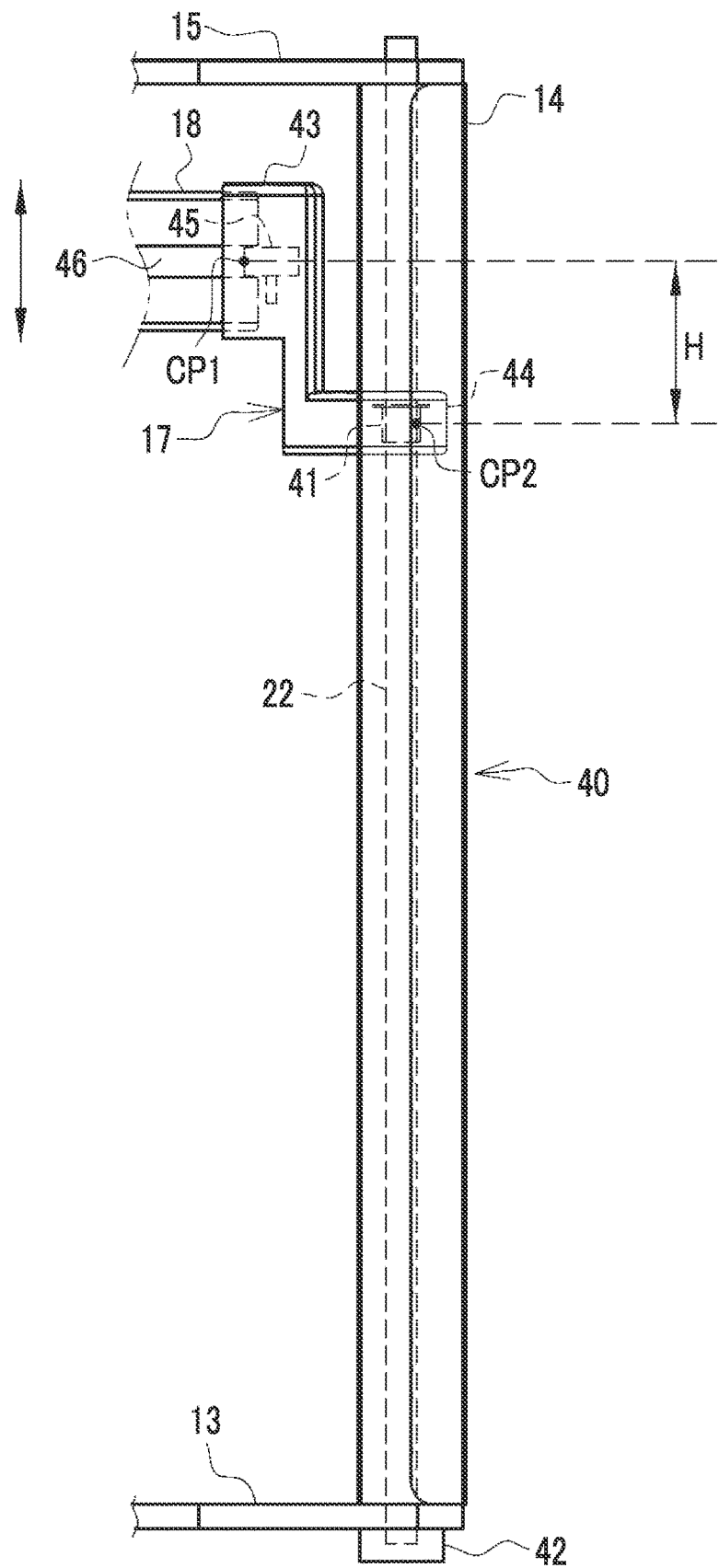
FIG. 7 is a diagram showing an elevation mechanism.

As shown in FIG. 7 as an example, the elevation mechanism 40 that moves up and down the connecting member 17 and the frame 18 in the vertical direction is a ball screw mechanism configured of the above-described screw shaft 22, a ball-containing nut 41 that is screwed with the screw shaft 22, a motor 42 for elevation that rotates the screw shaft 22, and the like. The motor 42 for elevation is attached to the back surface of the stage 13. A height position of the frame 18 is derived from a rotation orientation and a rotation speed of the motor 42 for elevation.

The connecting member 17 has a first connecting part 43 that is connected to the frame 18, and a second connecting part 44 that is connected to the column 14. The first connecting part 43 protrudes to the frame 18 side, the second connecting part 44 protrudes to the column 14 side, and the connecting member 17 has a Z shape as a whole. The first connecting part 43 incorporates a bearing 45. The bearing 45 is fitted into a guide groove 46 (also set FIG. 1 and the like) formed over the whole periphery of the frame 18. The bearing 45 rolls with the rotation of the frame 18. The second connecting part 44 incorporates the nut 41.

A first connection position CP1 of the first connecting part 43 with the frame 18 is higher by a height H than a second connection position CP2 of the second connecting part 44 with the column 14. Here, a point where a center of the bearing 45 is in contact with the guide groove 46 of the frame 18 is set as the first connection position CP1. A point where a center of the nut 41 is in contact with the screw shaft 22 is set as the second connection position CP2.

Figure 8:
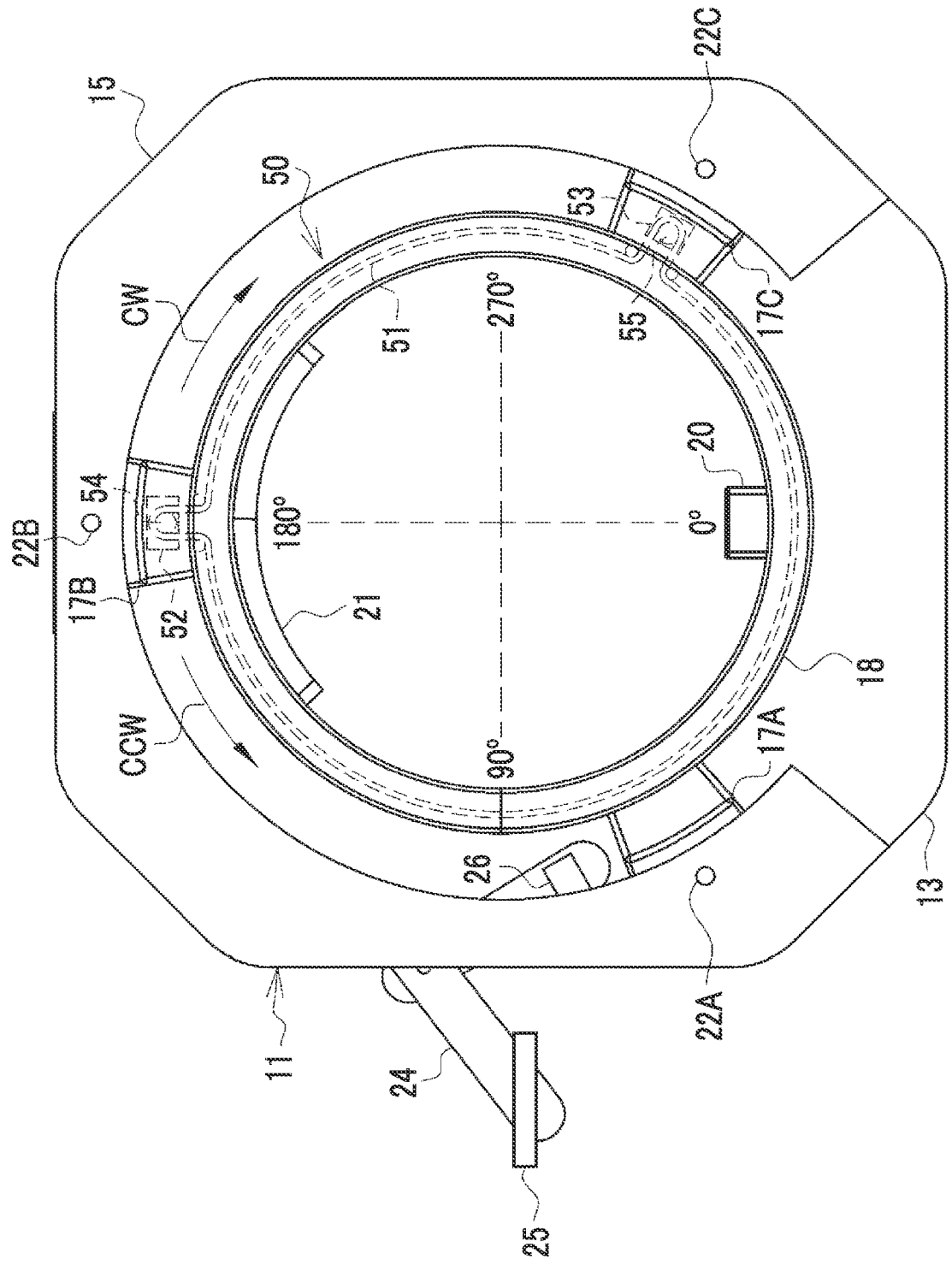
FIG. 8 is a diagram showing a rotation mechanism.

As shown in FIG. 8 as an example, a rotation mechanism 50 that rotates the frame 18 around the subject S is configured of a rotating belt 51 that is stretched around the whole periphery of the frame 18, a motor 52 for rotation, a potentiometer 53, and the like. The motor 52 for rotation is incorporated in the connecting member 17C and is connected to a part of the rotating belt 51 led out from the frame 18 through a pulley 54. With the drive of the motor for rotation 52, the frame 18 rotates in a clockwise rotation (right-handed rotation) direction CW and a counterclockwise rotation (left-handed rotation) direction CCW. The potentiometer 53 is incorporated in the connecting member 17B and is connected to a part of the rotating belt 51 led out from the frame 18 through a pulley 55. The potentiometer 53 has a variable resistor a resistance value of which varies depending on the rotation position of the frame 18 and outputs a voltage signal depending on the rotation position of the frame 18. The rotation position of the frame 18 is derived by the voltage signal from the potentiometer 53. The elevation mechanism 40 and the rotation mechanism 50 are an example of a "moving mechanism" according to the technique of the present disclosure.

Figure 9:
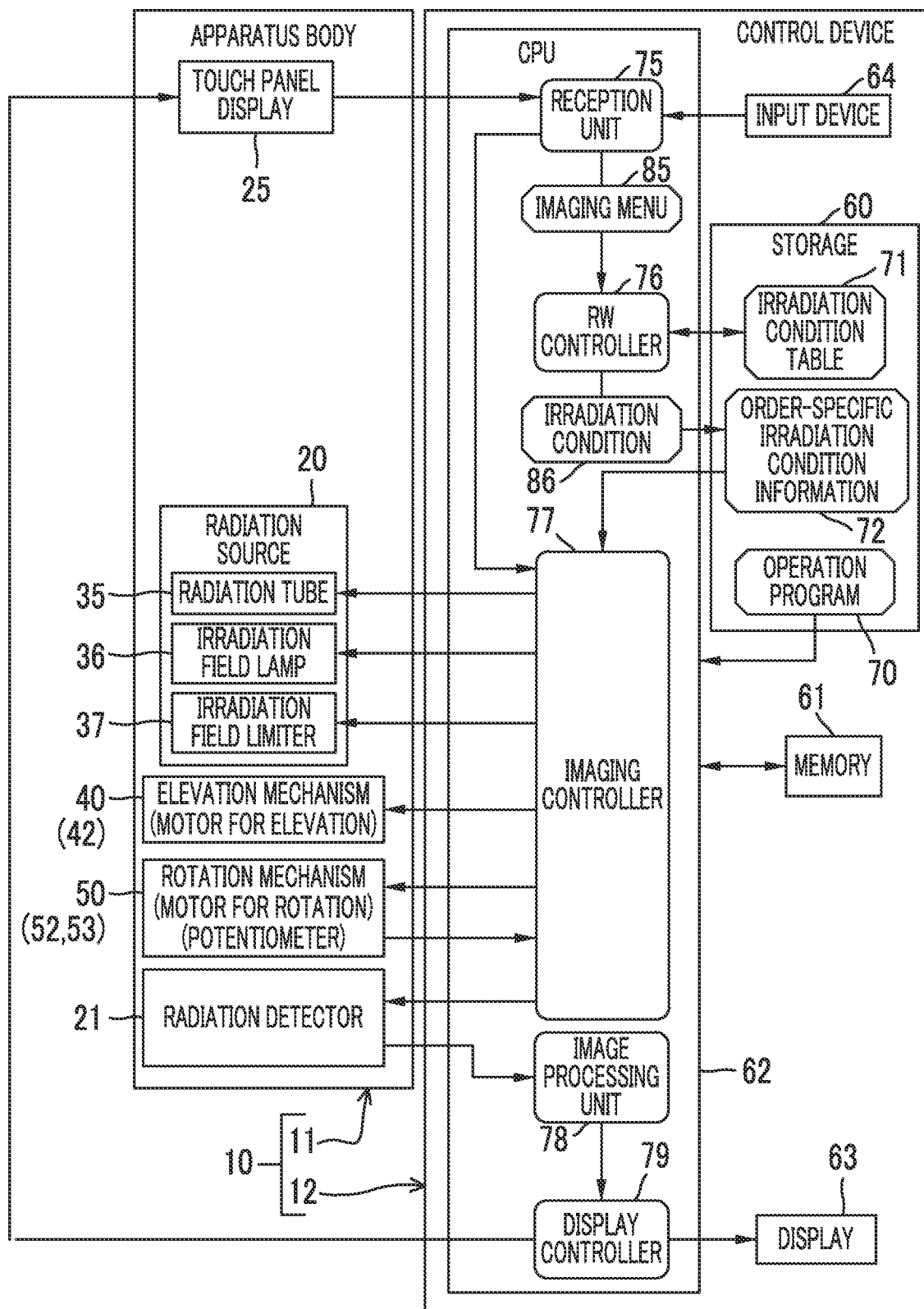
FIG. 9 is a block diagram showing a processing unit of a CPU of a control device.

As shown in FIG. 9 as an example, a computer configuring the control device 12 comprises a storage 60, a memory 61, a central processing unit (CPU) 62, a display 63, an input device 64, and the like. The CPU 62 is an example of a "processor" according to the technique of the present disclosure.

The storage 60 is a hard disk drive that is incorporated in the computer configuring the control device 12 or is connected to the computer through a cable or a network. Otherwise, the storage 60 is a disk array in which a plurality of hard disk drives are mounted in rows. In the storage 60, a control program, such as an operating system, various application programs, and various kinds of data accompanied with such programs, and the like are stored. A solid state drive may be used instead of the hard disk drive.

The memory 61 is a work memory on which the CPU 62 executes processing. The CPU 62 loads the programs stored in the storage 60 to the memory 61 and executes processing depending on the programs. With this, the CPU 62 integrally controls each unit of the computer. The memory 61 may be incorporated in the CPU 62.

The display 63 displays various screens. Various screens are provided with an operation function by a graphical user interface (GUI). The computer configuring the control device 12 receives an input of an operation instruction from the input device 64 through various screens. The input device 64 is a keyboard, a mouse, a touch panel, a microphone for voice input, and the like.

An operation program 70 is stored in the storage 60. The operation program 70 is an application program that causes the computer to function as the control device 12. The operation program 70 is an example of an "operation program for a medical image capturing apparatus" according to the technique of the present disclosure. In the storage 60, in addition to the operation program 70, an irradiation condition table 71, order-specific irradiation condition information 72, and the like are stored.

In a case where the operation program 70 is started, the CPU 62 of the control device 12 functions as a reception unit 75, a read write (hereinafter, abbreviated as RW) controller 76, an imaging controller 77, an image processing unit 78, and a display controller 79 in cooperation with the memory 61 and the like.

The reception unit 75 receives various operation instructions input from the operator through the touch panel display 25 and the apparatus body 11 and the input device 64. For example, the reception unit 75 receives an imaging menu 85. The reception unit 75 outputs the imaging menu 85 to the RW controller 76.

The RW controller 76 receives the imaging menu 85 from the reception unit 75. The RW controller 76 reads out an irradiation condition 86 of the radiation R corresponding to the received imaging menu 85 from the irradiation condition table 71. The RW controller 76 writes the irradiation condition 86 read out from the irradiation condition table 71 to the order-specific irradiation condition information 72.

The imaging controller 77 controls the operations of the radiation source 20 (radiation tube 35, irradiation field lamp 36, and irradiation field limiter 37), the elevation mechanism 40 (motor 42 for elevation), the rotation mechanism 50 (motor 52 for rotation and potentiometer 53), and the radiation detector 21. The imaging controller 77 reads out the irradiation condition 86 from the order-specific irradiation condition information 72. The imaging controller 77 drives the irradiation field limiter 37 depending on the irradiation condition 86 and adjusts the irradiation field. The imaging controller 77 drives the radiation tube 35 depending on the irradiation condition 86 and causes the emission of the radiation R from the radiation tube 35. The imaging controller 77 outputs a projection image detected in the radiation detector 21 with the irradiation of the radiation R from the radiation detector 21 to the image processing unit 78.

The image processing unit 78 receives the projection image from the radiation detector 21. The image processing unit 78 executes various kinds of image processing on the projection image. The image processing unit 78 executes reconstruction processing on a plurality of projection images after the image processing and generates a tomographic image TI. The image processing unit 78 outputs the projection images after the image processing or the tomographic image TI to the display controller 79.

The display controller 79 controls display of various kinds of information on the touch panel display 25 and the display 63. The display controller 79 receives the projection images or the tomographic image TI from the image processing unit 78. The display controller 79 displays the projection images or the tomographic image TI on the touch panel display 25 and the display 63.

The imaging menu 85 includes, for example, imaging order identification data (ID) and an imaging procedure (see FIG. 10). The imaging order ID is identification information of an imaging order issued by a physician who performs a medical examination using a tomographic image. The imaging procedure is configured of a posture of the subject S, such as upright and sitting, an imaging part, such as a head, a neck, and a spine, and an attribute of the subject S, such as an adult male and an adult female.

The imaging order is transmitted from a radiology information system (RIS) (not shown) to the control device 12. The control device 12 displays a list of imaging orders on the display 63 under the control of the display controller 79. The operator views the list of imaging orders to confirm the contents. Subsequently, the control device 12 displays an imaging menu corresponding to the imaging order on the display 63 in a settable form. The operator selects and inputs the imaging menu depending on the imaging order by operating the input device 64.

As shown in FIG. 10 as an example, the irradiation condition 86 is registered in the irradiation condition table 71 for each imaging procedure. In the irradiation condition 86, a tube voltage and a tube current that are applied to the radiation tube 35, and an irradiation time of the radiation R are included. Though not shown, a size of the irradiation field is also included in the irradiation condition 86. The irradiation condition 86 can be subjected to fine adjustment with the hand of the operator. Instead of the tube current and the irradiation time, a tube current-irradiation time product, a so-called mAs value may be used as the irradiation condition 86.

In the irradiation condition table 71, a scout imaging position and a fourth rotation position are also registered for each imaging procedure. The scout imaging position is a set of a reference height position and a second or third rotation position of the frame 18 in scout imaging. The reference height position indicates the height of the frame 18 in a case where the front surface of the stage 13 is set to 0 cm. The second rotation position is a position where the radiation source 20 confronts the subject S, that is, a position of 0°. The third rotation position is a position where the radiation source 20 faces a right side surface of the subject S, that is, a position of 90°. A position of 270° where the radiation source 20 faces the left side surface of the subject S may be set as the third rotation position.

Here, scout imaging is preliminary radiography that is performed to confirm positioning of the subject S before main imaging for capturing a plurality of projection images of each predetermined angle to generate the tomographic image TI. In scout imaging, after the frame 18 is at the reference height position and the second rotation position or the third rotation position, the irradiation of the radiation R with a dose lower than main imaging is performed to obtain one projection image. Hereinafter, the projection image obtained by scout imaging is described as a scout image SI (see FIG. 14).

The imaging procedure includes an imaging procedure in which only the second rotation position is registered and an imaging procedure in which both the second rotation position and the third rotation position are registered. For example, in an imaging procedure of "upright head adult male", only the second rotation position is registered. On the other hand, for example, in an imaging procedure of "sitting spine adult male", both the second rotation position and the third rotation position are registered.

The fourth rotation position is a rotation start position of the frame 18 in main imaging. For example, in an imaging procedure of "upright head adult male", the position of 0° is registered as the fourth rotation position. For example, in an imaging procedure of "sitting spine adult male", the position of 90° is registered as the fourth rotation position.

Though not shown, in the order-specific irradiation condition information 72, the irradiation condition 86, the scout imaging position, and the fourth rotation position are registered for each imaging order ID. The imaging controller 77 reads out the irradiation condition 86, the scout imaging position, and the fourth rotation position corresponding to a next imaging order ID from the order-specific irradiation condition information 72 and controls the operation of each unit depending on the read-out irradiation condition 86, scout imaging position, and fourth rotation position.

As shown in FIG. 11 as an example, in leading the subject S inside the apparatus body 11, the frame 18 is moved to the retreat height position by the elevation mechanism 40 and is rotated to the first rotation position by the rotation mechanism 50 under the control of the imaging controller 77. The retreat height position is set on an upper end side of the column 14. In more detail, the retreat height position is a position of a highest point in an elevation range of the frame 18. In the example, the position of the highest point in the elevation range of the frame 18 is a position of a substantially upper end of the column 14, and is a position where the second connecting part 44 of the connecting member 17 is in contact with the back surface of the top plate 15. Incidentally, a position of a lowest point in the elevation range of the frame 18 is a position of a substantially lower end of the column 14 and is a position where the second connecting part 44 is in contact with the front surface of the stage 13. The first rotation position is a position of 60° where the entire radiation source 20 overlaps the column 14A as also shown in FIG. 12 in which the state of FIG. 11 is viewed from above. The operator leads the subject S inside the apparatus body 11 in such a state with a space between the columns 14A and 14C as an entrance and positions the subject S. An arrow shown in FIGS. 11 and 12 indicates a direction in which the subject S is led inside the apparatus body 11.

Figure 13:
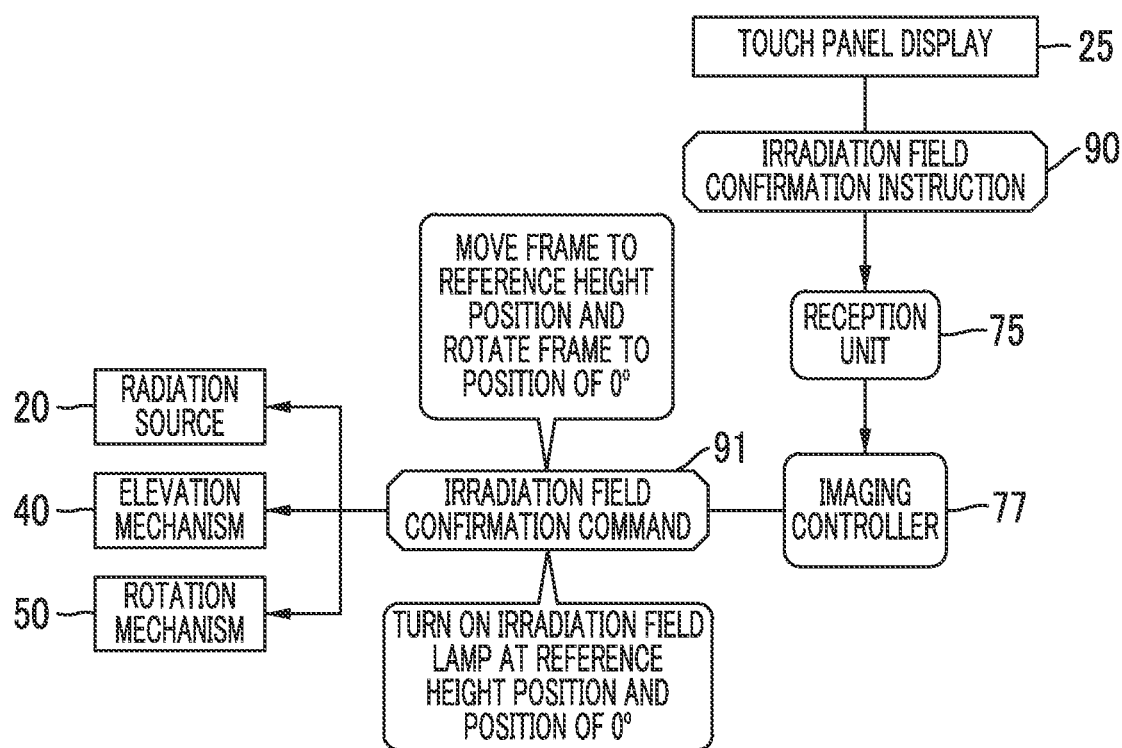
FIG. 13 is a diagram showing the outline of processing in a case where an irradiation field confirmation instruction for confirming to an irradiation field of radiation is input.

As shown in FIG. 13 as an example, after positioning the subject S inside the apparatus body 11, the operator stays in the installation place of the apparatus body 11 and operates the touch panel display 25 to input an irradiation field confirmation instruction 90 for confirming the irradiation field of the radiation R. The reception unit 75 receives the irradiation field confirmation instruction 90 and outputs information indicating the reception of the irradiation field confirmation instruction 90 to the imaging controller 77. The imaging controller 77 outputs an irradiation field confirmation command 91 depending on the irradiation field confirmation instruction 90 to the radiation source 20, the elevation mechanism 40, and the rotation mechanism 50.

The content of the irradiation field confirmation command 91 is that the frame 18 is moved to the reference height position and the frame 18 is rotated to the position of 0°. Furthermore, the content of the irradiation field confirmation command 91 is that the irradiation field lamp 36 is turned on at the reference height position and the position of 0°. The elevation mechanism 40 drives the motors 42 for elevation to rotate the screw shafts 22, thereby moving the frame 18 to the reference height position. The rotation mechanism 50 drives the motor 52 for rotation to rotate the rotating belt 51, thereby rotating the frame 18 to the position of 0°. The radiation source 20 drives the irradiation field limiter 37 to adjust the irradiation field to an irradiation field depending on the irradiation condition 86, and then, turns on the irradiation field lamp 36 to irradiate the irradiation field with visible light.

The operator visually recognizes visible light from the irradiation field lamp 36 and determines whether or not the height position of the frame 18 and the positioning of the subject S are appropriate for imaging. In a case where determination is made that the height position of the frame 18 and the positioning of the subject S are not appropriate for imaging, the operator operates the touch panel display 25 to adjust the height position of the frame 18 or performs the positioning of the subject S again. In a case where determination is made that the height position of the frame 18 and the positioning of the subject S are appropriate for imaging, the operator operates the touch panel display 25 to input a turn-off instruction of the irradiation field lamp 36. The reception unit 75 receives the turn-off instruction and outputs information indicating the reception of the turn-off instruction to the imaging controller 77. The imaging controller 77 turns off the irradiation field lamp 36 in response to the turn-off instruction.

Figure 14:
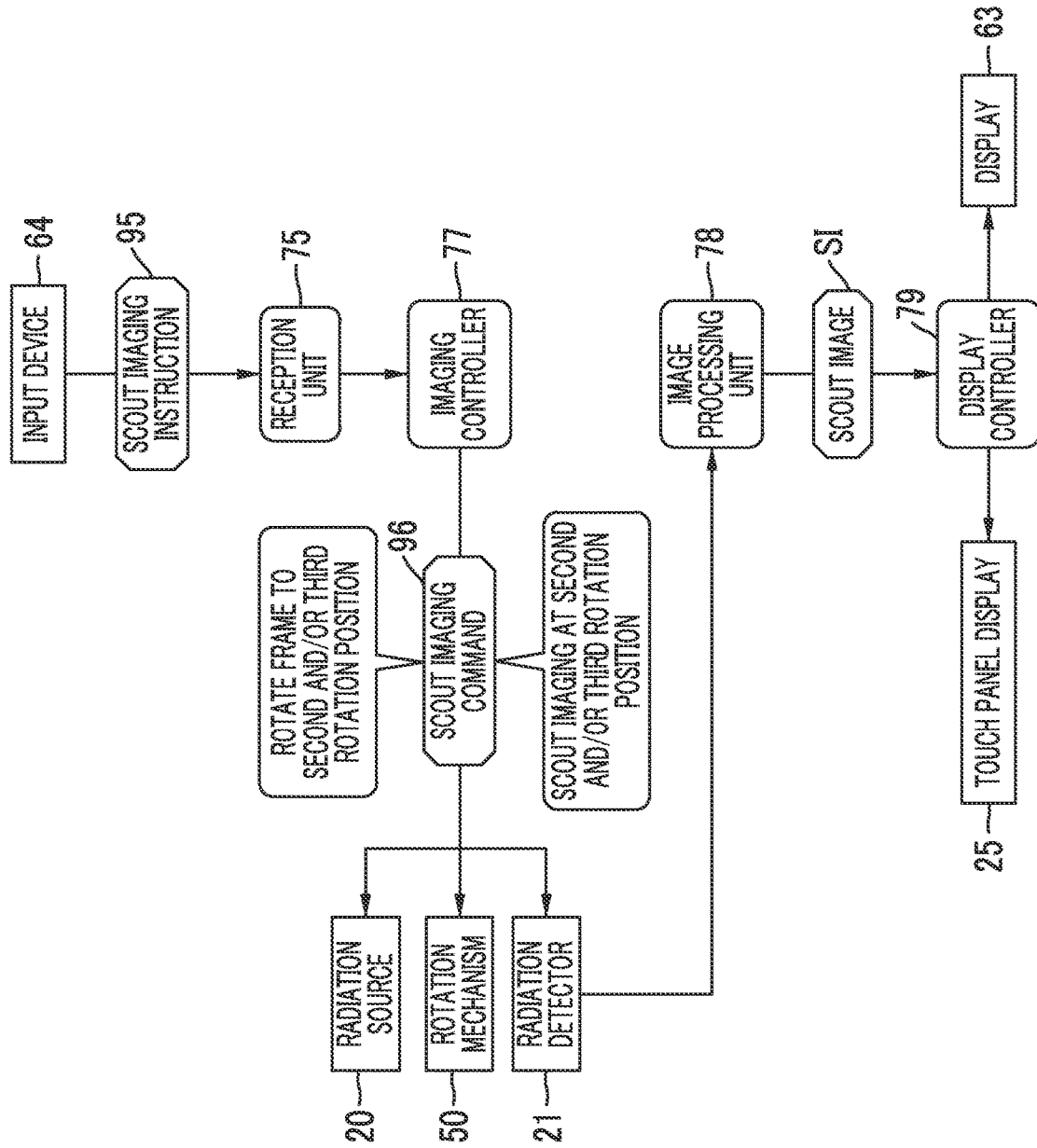
FIG. 14 is a diagram showing the outline of processing in a case where a scout imaging instruction for performing scout imaging is input.

As shown in FIG. 14 as an example, after confirming the irradiation field of the radiation R, the operator moves to the installation place to the control device 12 and operates the input device 64 to input a scout imaging instruction 95 for scout imaging. The reception unit 75 receives the scout imaging instruction 95 and outputs information indicating the reception of the scout imaging instruction 95 to the imaging controller 77. The imaging controller 77 outputs a scout imaging command 96 depending on the scout imaging instruction 95 to the radiation source 20, the radiation detector 21, and the rotation mechanism 50.

Figure 15:
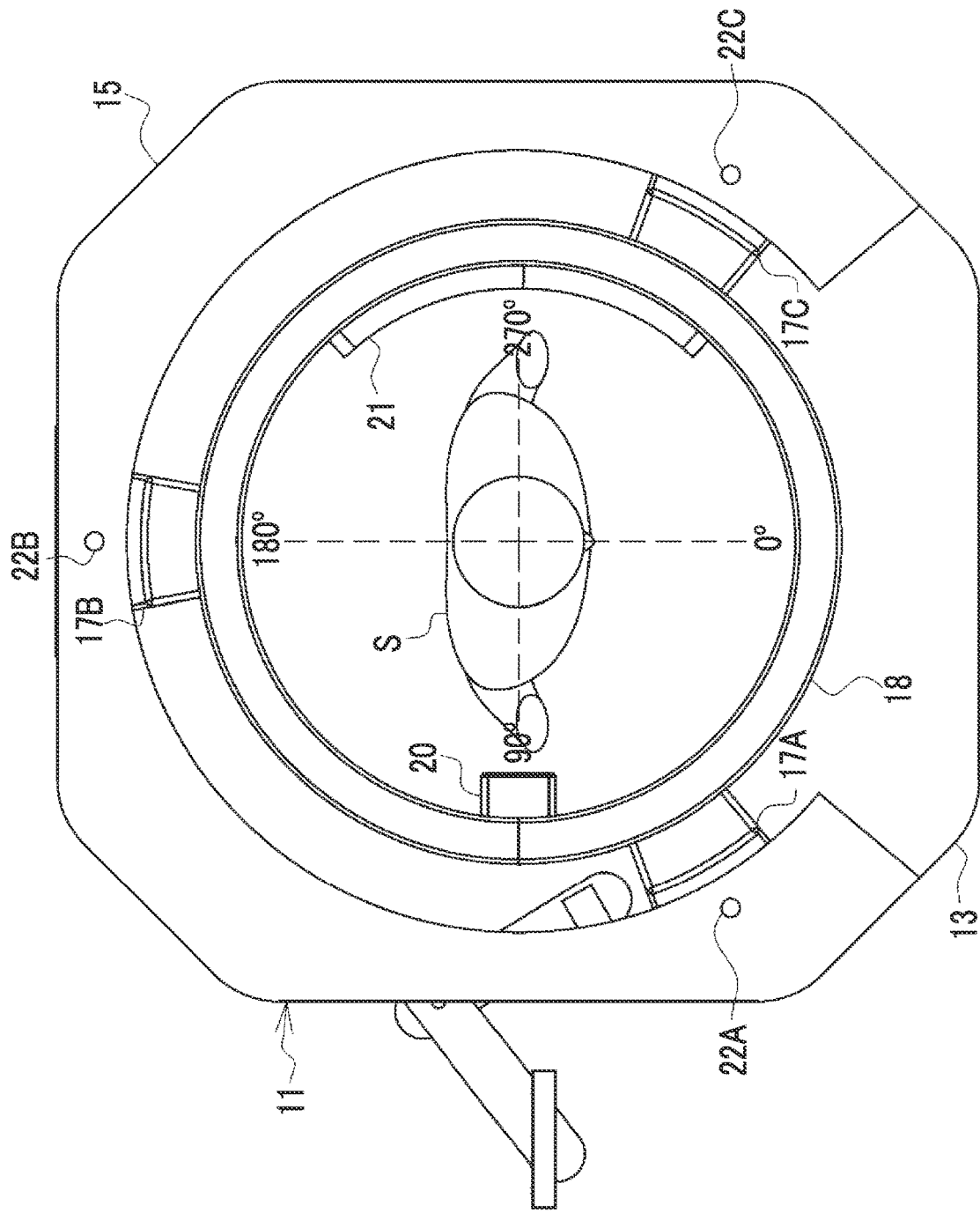
FIG. 15 is a diagram showing a state in which the frame is rotated to a third rotation position.

The content of the scout imaging command 96 is that the height position is maintained in a state at the time of the confirmation of the irradiation field of the radiation R, and the frame 18 is rotated to the second rotation position and/or the third rotation position. Furthermore, the content of the scout imaging command 96 is that scout imaging is performed at the second rotation position and/or the third rotation position. The rotation mechanism 50 drives the motor 52 for rotation to rotate the rotating belt 51, thereby rotating the frame 18 to the second rotation position and/or the third rotation position. FIG. 15 shows a state in which the frame 18 is rotated to the position of 90° as the third rotation position.

The radiation source 20 drives the radiation tube 35 to irradiate the subject S with the radiation R for scout imaging. The radiation detector 21 detects the radiation R transmitted through the subject S to obtain a projection image. The radiation detector 21 outputs the projection image to the image processing unit 78.

The image processing unit 78 executes various kinds of image processing on the projection image from the radiation detector 21 to generate a scout image SI. The image processing unit 78 outputs the scout image SI to the display controller 79. The display controller 79 displays the scout image SI on the touch panel display 25 and the display 63.

The operator views the scout image SI on the display 63 and determines again whether or not the height position of the frame 18 and the positioning of the subject S are appropriate for imaging. In a case where determination is made that the height position of the frame 18 and the positioning of the subject S are not appropriate for imaging with the scout image SI, the operator returns to the installation place of the apparatus body 11, turns on the irradiation field lamp 36 again, and adjusts the height position of the frame 18 or performs the positioning of the subject S again.

Figure 16:
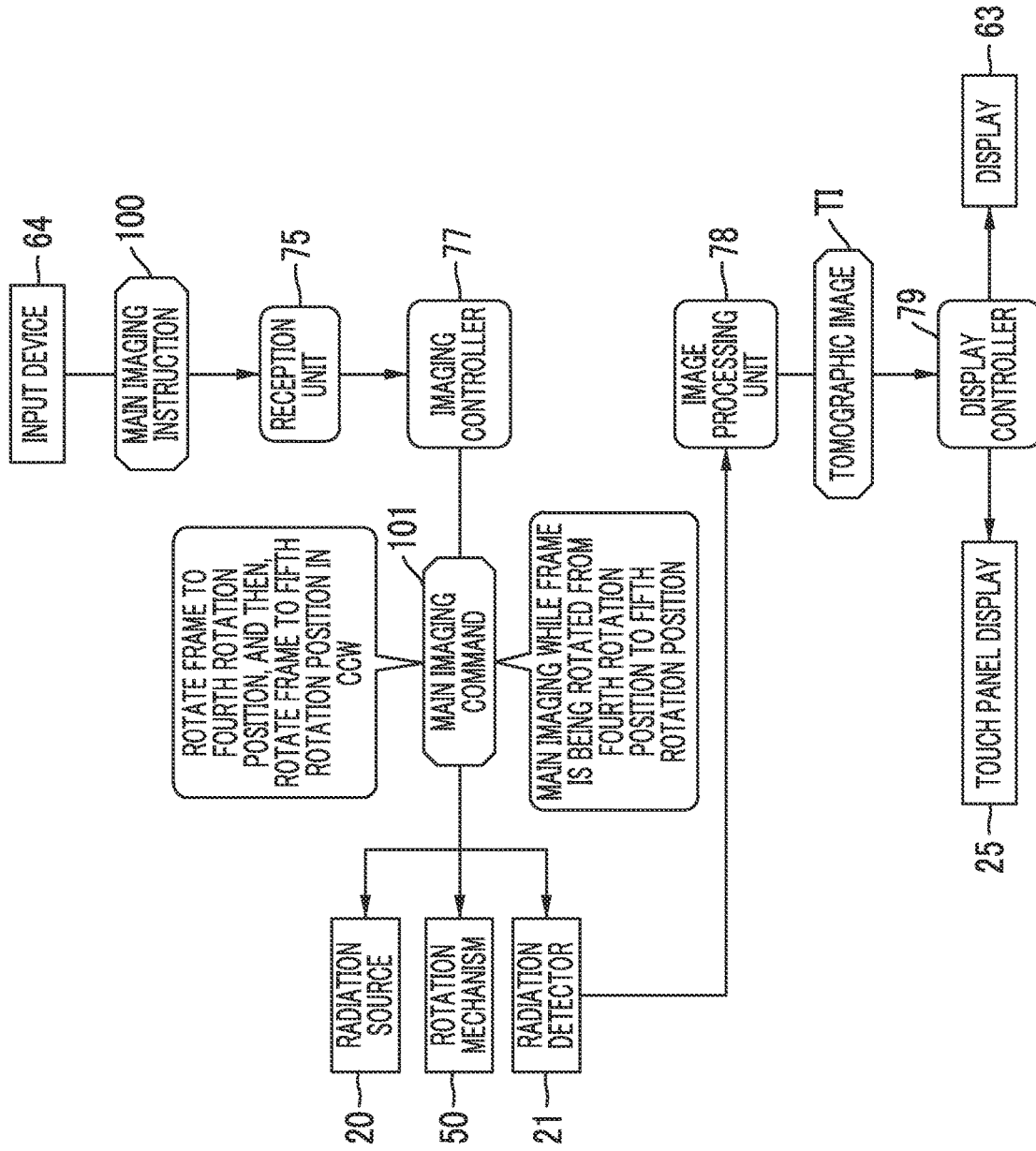
FIG. 16 is a diagram showing the outline of processing in a case where a main imaging instruction for main imaging is input.

As shown in FIG. 16 as an example, in a case where determination is made that the height position of the frame 18 and the positioning of the subject S are appropriate for imaging with the scout image SI, the operator operates the input device 64 to input a main imaging instruction 100 for main imaging. The reception unit 75 receives the main imaging instruction 100 and outputs information indicating the reception of the main imaging instruction 100 to the imaging controller 77. The imaging controller 77 outputs a main imaging command 101 depending on the main imaging instruction 100 to the radiation source 20, the radiation detector 21, and the rotation mechanism 50.

The content of the main imaging command 101 is that the height position is maintained in a state at the time of the end of scout imaging, the frame 18 is rotated to the fourth rotation position, and then, the frame 18 is rotated to a fifth rotation position at a first set rotation speed set in advance in a counterclockwise rotation direction CCW. Furthermore, the content of the main imaging command 101 is that main imaging is performed while the frame 18 is being rotated from the fourth rotation position to the fifth rotation position. The rotation mechanism 50 drives the motor 52 for rotation to rotate the rotating belt 51, thereby first rotating the frame 18 to the fourth rotation position. Thereafter, the rotation mechanism 50 rotates the frame 18 to the fifth rotation position at the first set rotation speed in the counterclockwise rotation direction CCW. The fifth rotation position is a position where the frame 18 is rotated by 225° from the fourth rotation position in the counterclockwise rotation direction CCW in the example.

Figure 17:
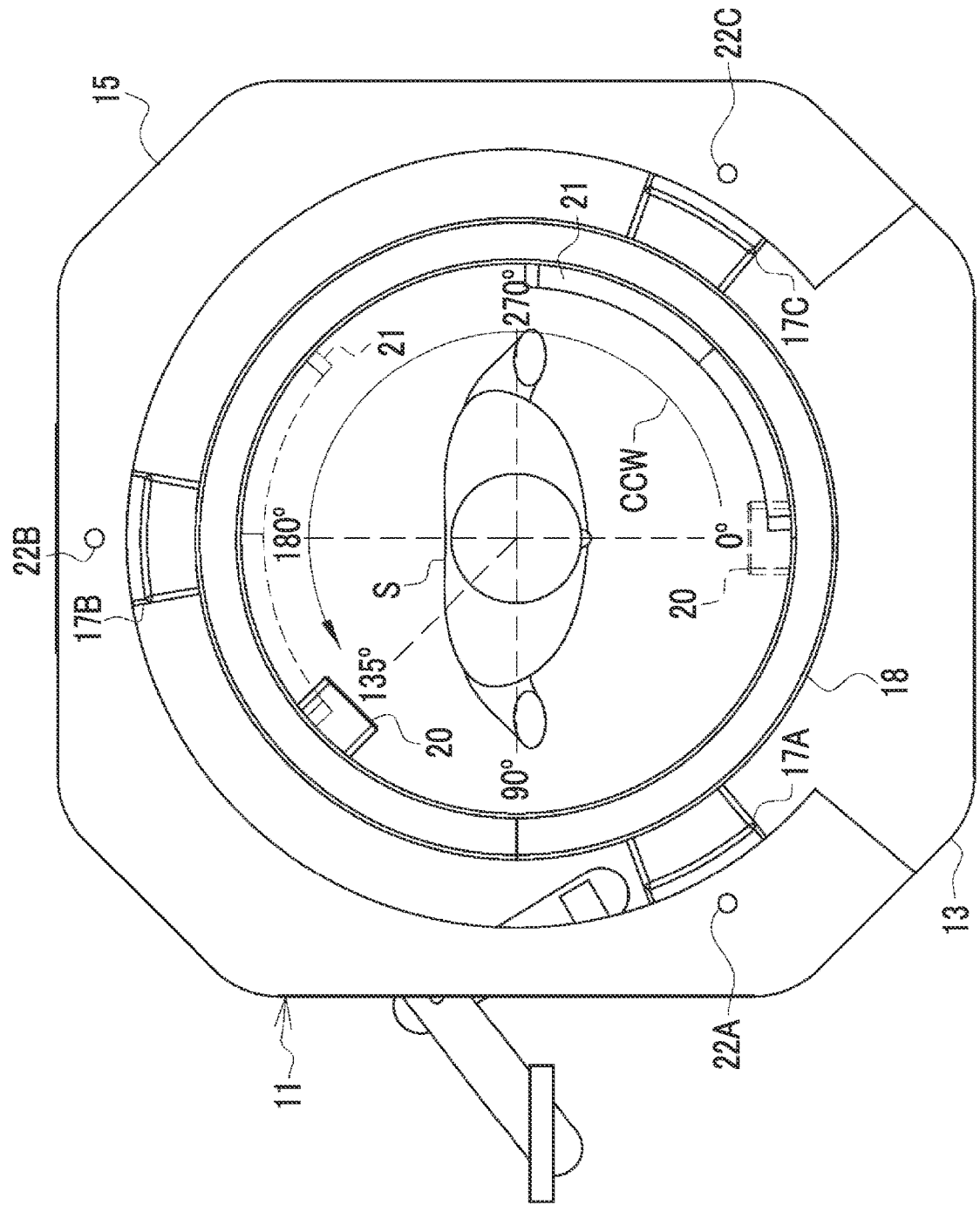
FIG. 17 is a diagram showing a scene where the frame is rotated from a fourth rotation position to a fifth rotation position.

FIG. 17 shows a case where the fourth rotation position is the position of 0°. In this case, the fifth rotation position is a position of 135° where the frame 18 is rotated by 225° from the position of 0° in the counterclockwise rotation direction CCW. Though not shown, the fifth rotation position in a case where the fourth rotation position is 90° is a position of 225°, and the fifth rotation position in a case where the fourth rotation position is 180° is a position of 315°.

The radiation source 20 drives the radiation tube 35 at each predetermined angle to irradiate the subject S with the radiation R for main imaging depending on the irradiation condition 86 at each predetermined angle. The radiation detector 21 detects the radiation R transmitted through the subject S at each predetermined angle to obtain a plurality of projection images. The radiation detector 21 sequentially outputs a plurality of projection images to the image processing unit 78.

The image processing unit 78 executes reconstruction processing on a plurality of projection images from the radiation detector 21 to generate a tomographic image TI. The image processing unit 78 outputs the tomographic image TI to the display controller 79. The display controller 79 displays the tomographic image TI on the touch panel display 25 and the display 63.

The operator views the tomographic image TI on the display 63 and determines whether or not re-imaging of the tomographic image TI is required. In a case where determination is made that re-imaging of the tomographic image TI is required, the operator operates the input device 64 to input the main imaging instruction 100 again.

Figure 18:
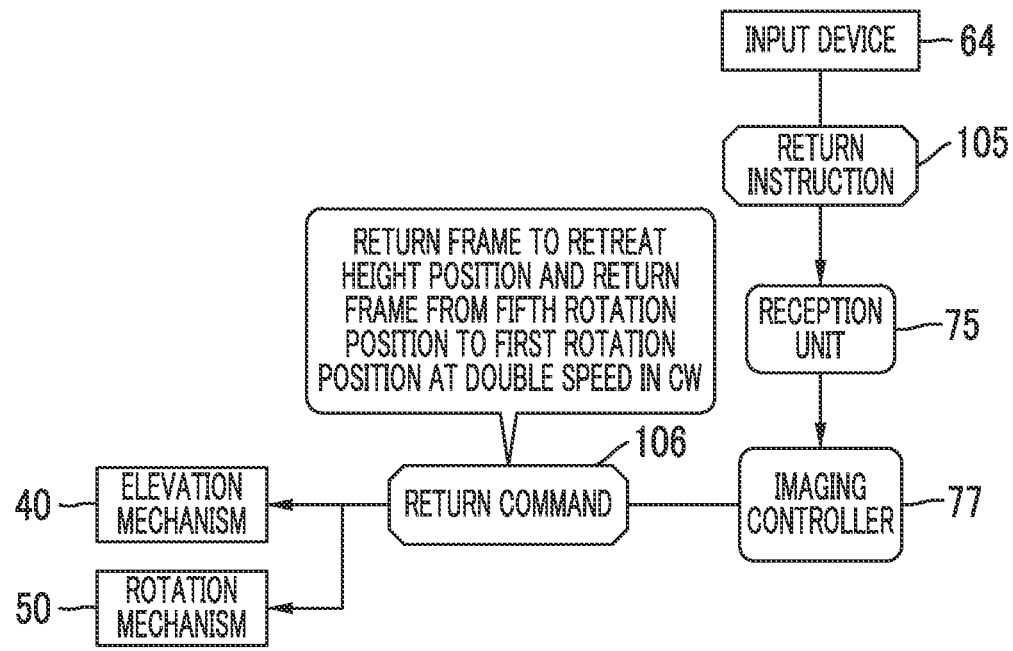
FIG. 18 is a diagram showing the outline of processing in a case where a return instruction for returning the frame to the retreat height position and the first rotation position is input.

As shown in FIG. 18 as an example, in a case where determination is made that re-imaging of the tomographic image TI is not required, the operator operates the input device 64 to input a return instruction 105 for returning the frame 18 to the retreat height position and the first rotation position. The reception unit 75 receives the return instruction 105 and outputs information indicating the reception of the return instruction 105 to the imaging controller 77. The imaging controller 77 outputs a return command 106 depending on the return instruction 105 to the elevation mechanism 40 and the rotation mechanism 50.

The content of the return command 106 is that the frame 18 is returned to the retreat height position, and the frame 18 is returned from the fifth rotation position to the first rotation position at a second set rotation speed of a double speed of the first set rotation speed in a clockwise rotation direction CW. The elevation mechanism 40 drives the motors 42 for elevation to rotate the screw shafts 22, thereby returning the frame 18 to the retreat height position. The rotation mechanism 50 drives the motor 52 for rotation to rotate the rotating belt 51, thereby returning the frame 18 from the fifth rotation position to the first rotation position at the second set rotation speed in the clockwise rotation direction CW.

Figure 19:
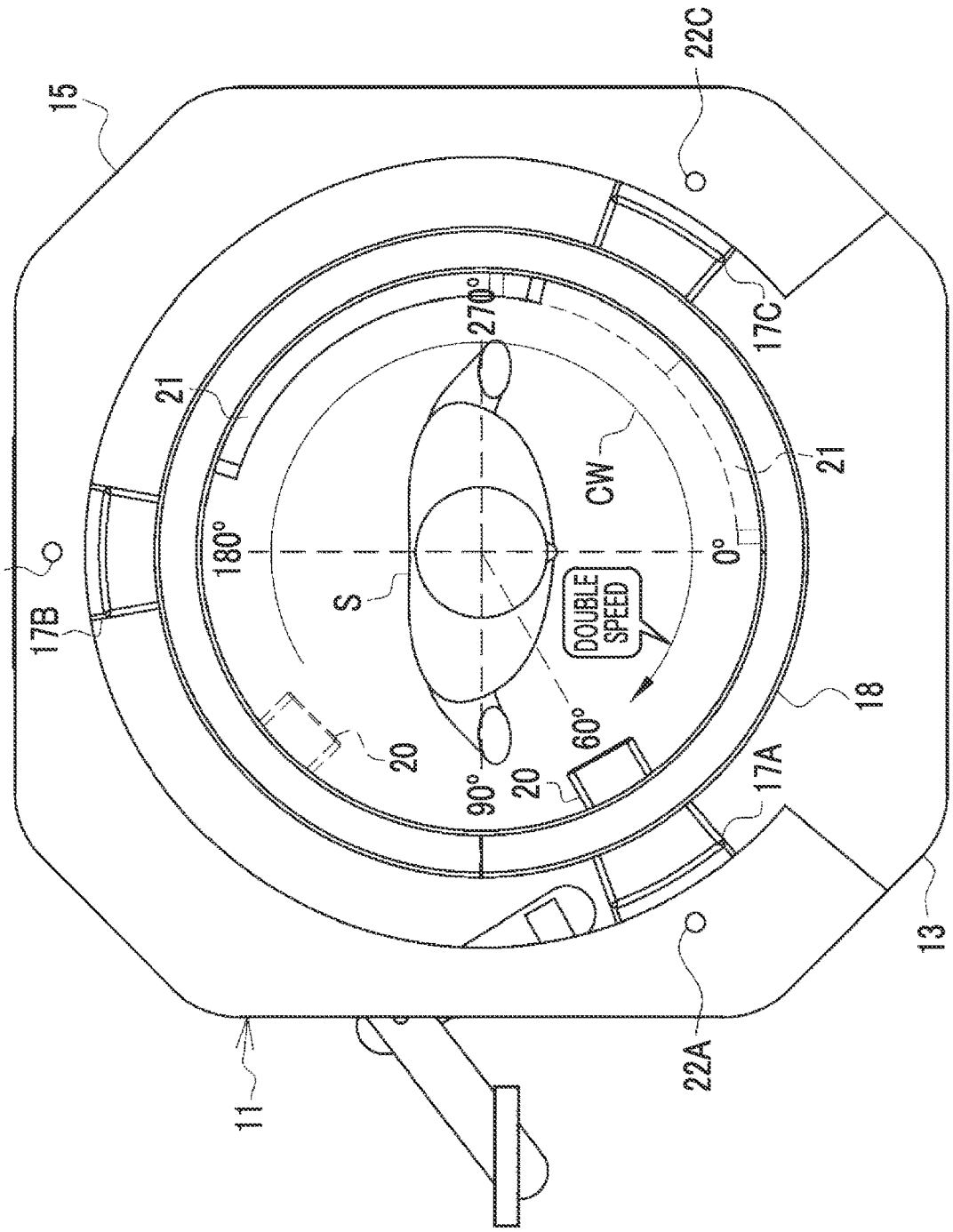
FIG. 19 is a diagram showing a scene where the frame is returned from the fifth rotation position to the first rotation position.

FIG. 19 shows a case where the fifth rotation position is the position of 135°. In this case, the rotation mechanism 50 returns the frame 18 from the position of 135° as the fifth rotation position to the position of 60° as the first rotation position at the second set rotation speed in the clockwise rotation direction CW. After the frame 18 is returned to the retreat height position, and the frame 18 is returned to the first rotation position, the operator retreats the subject S from the inside of the apparatus body 11.

Figure 20:
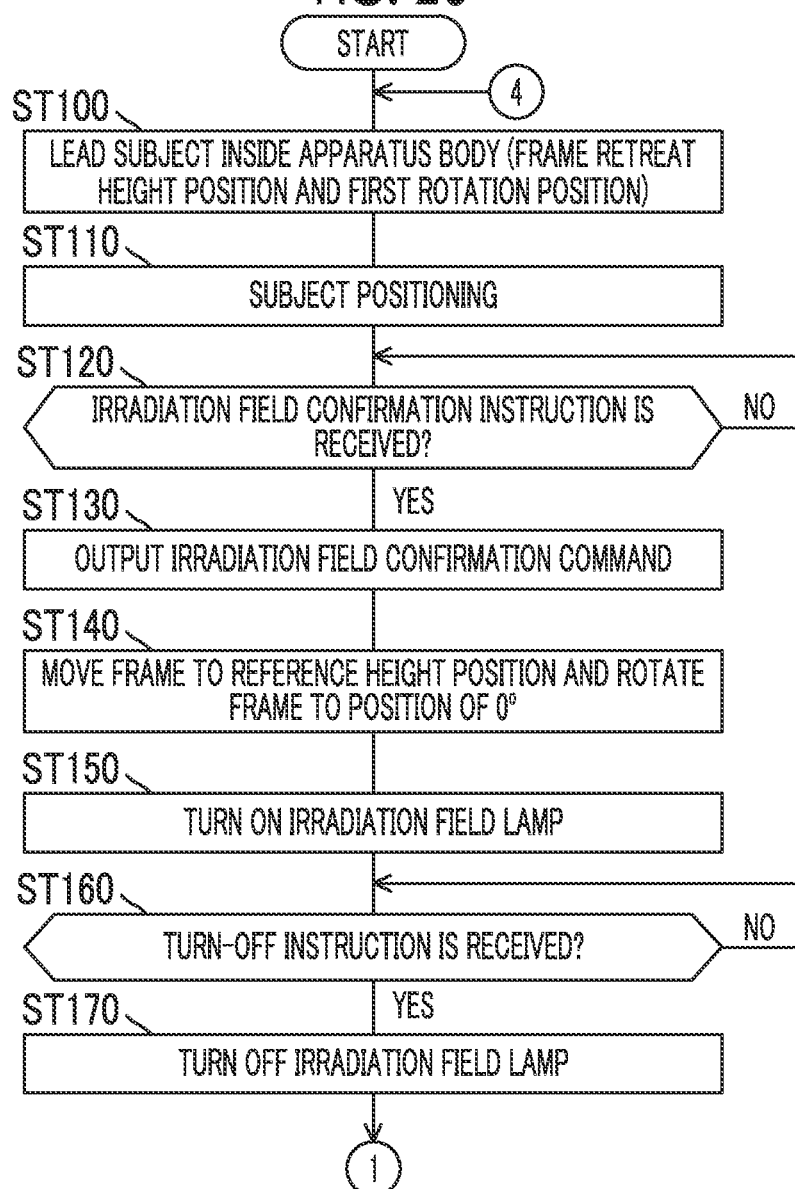
FIG. 20 is a flowchart illustrating an imaging procedure of a tomographic image by the CT apparatus.
Figure 21:
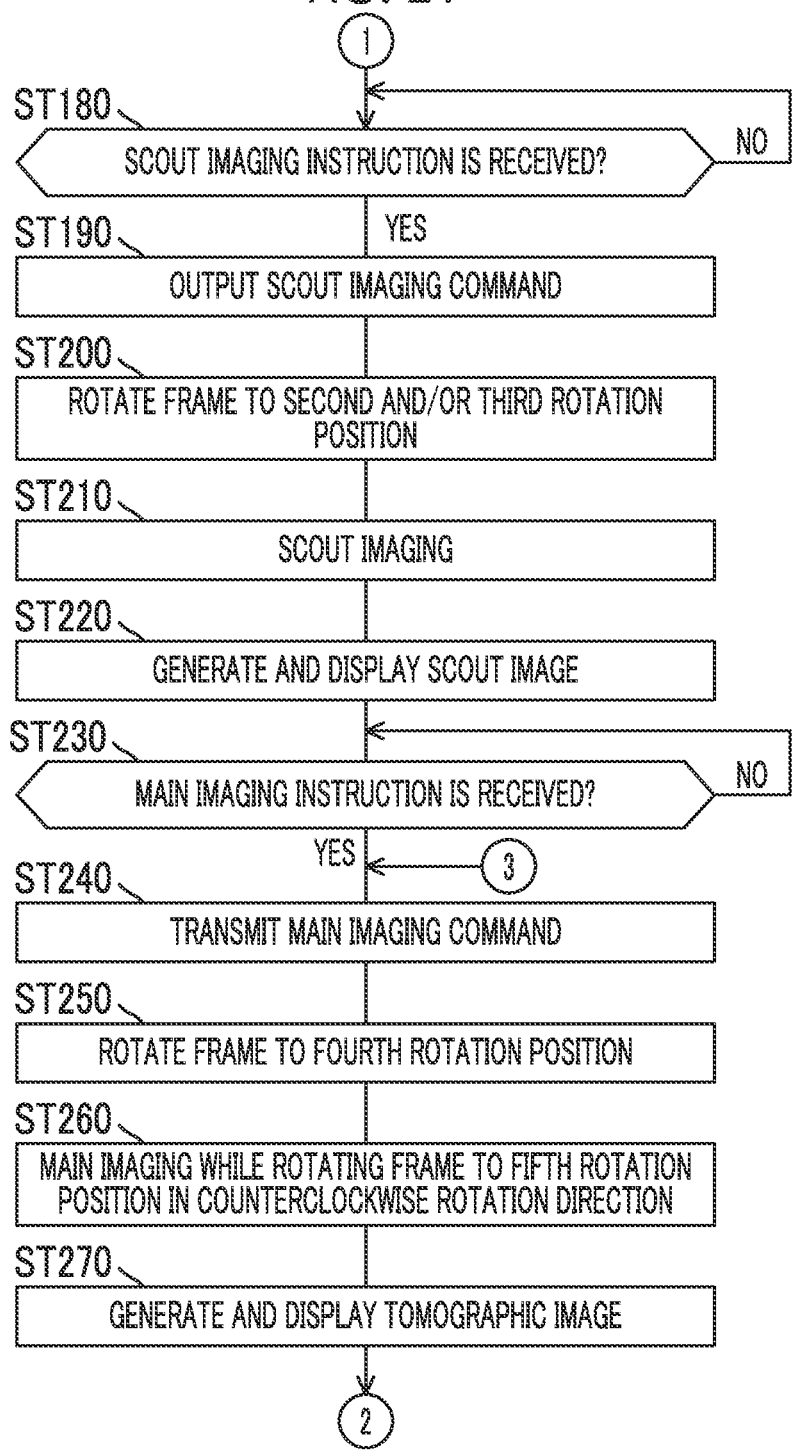
FIG. 21 is a flowchart illustrating the imaging procedure of the tomographic image by the CT apparatus.
Figure 22:
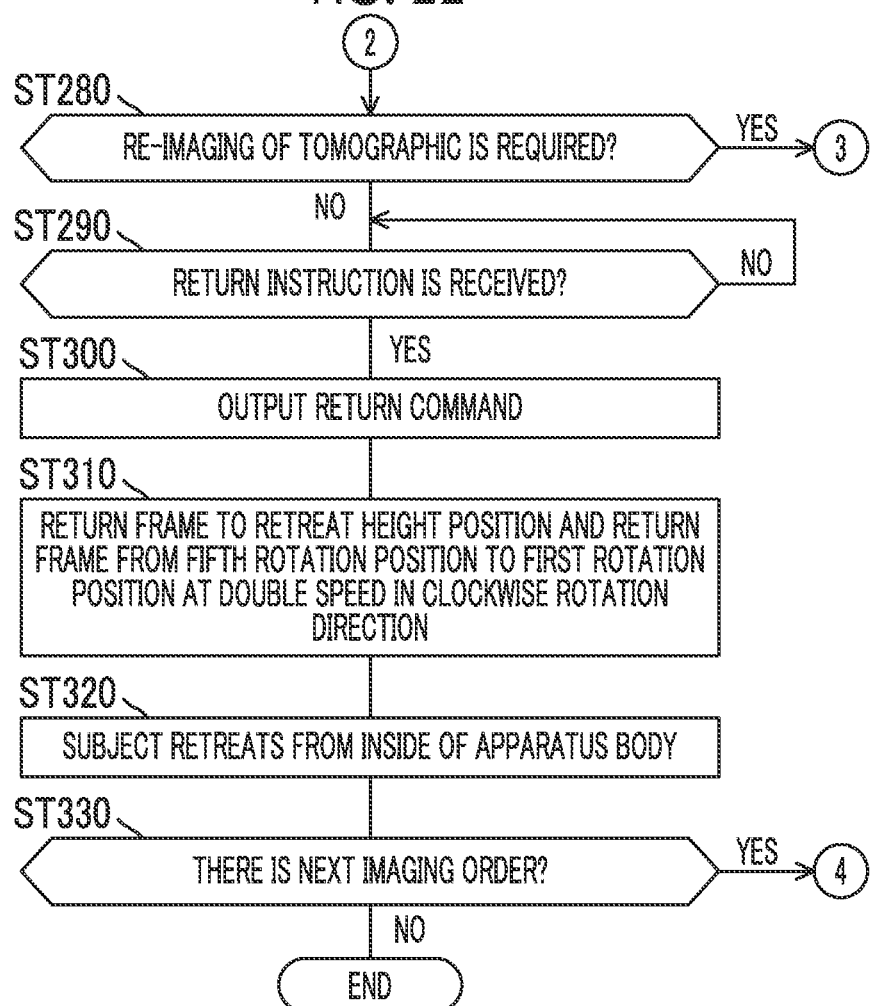
FIG. 22 is a flowchart illustrating the imaging procedure of the tomographic image by the CT apparatus.

Next, the operations of the above-described configuration will be described referring to flowcharts shown in FIGS. 20 to 22 as an example. In a case where the operation program 70 is started, as shown in FIG. 9, the CPU 62 of the control device 12 functions as the reception unit 75, the RW controller 76, the imaging controller 77, the image processing unit 78, and the display controller 79.

First, as shown in FIGS. 11 and 12, in a state in which the frame 18 is moved to the retreat height position, and the frame 18 is rotated to the first rotation position, the subject S is led inside the apparatus body 11 by the operator (Step ST100). Then, the subject S is positioned by the operator (Step ST110).

As shown in FIG. 13, after the positioning of the subject S, the operator inputs the irradiation field confirmation instruction 90 through the touch panel display 25. The irradiation field confirmation instruction 90 is received in the reception unit 75 (in Step ST120, YES). With this, the irradiation field confirmation command 91 is output from the imaging controller 77 to the radiation source 20 and the like (Step ST130).

The elevation mechanism 40 is operated by the irradiation field confirmation command 91 and the frame 18 is moved to the reference height position. The rotation mechanism 50 is operated and the frame 18 is rotated to the position of 0° (Step ST140). In addition, the irradiation field limiter 37 is driven to adjust the irradiation field to the irradiation field depending on the irradiation condition 86, then, the irradiation field lamp 36 is turned on, and the irradiation field is irradiated with visible light (Step ST150).

The operator determines whether or not the height position of the frame 18 and the positioning of the subject S are appropriate for imaging with reference to visible light from the irradiation field lamp 36. In a case where the height position of the frame 18 and the positioning of the subject S are not appropriate for imaging, the operator adjusts the height position of the frame 18 or performs the positioning of the subject S again. In a case where the height position of the frame 18 and the positioning of the subject S are appropriate for imaging, the operator inputs the turn-off instruction of the irradiation field lamp 36 through the touch panel display 25. The turn-off instruction is received in the reception unit 75 (in Step ST160, YES). Then, the imaging controller 77 turns off the irradiation field lamp 36 (Step ST170).

As shown in FIG. 14, after the confirmation of the irradiation field of the radiation R, the operator inputs the scout imaging instruction 95 through the input device 64. The scout imaging instruction 95 is received in the reception unit 75 (in Step ST180, YES). With this, the scout imaging command 96 is output from the imaging controller 77 to the radiation source 20 and the like (Step ST190).

As shown in FIG. 15, the rotation mechanism 50 is operated by the scout imaging command 96, and the frame 18 is rotated to the second rotation position and/or the third rotation position (Step ST200). In addition, the subject S is irradiated with the radiation R for scout imaging from the radiation tube 35, and the radiation detector 21 detects the radiation R transmitted through the subject S to obtain the projection image (Step ST210).

The projection image obtained in the radiation detector 21 is subjected to various kinds of image processing in the image processing unit 78 and generates the scout image SI. The scout image SI is displayed on the touch panel display 25 and the display 63 under the control of the display controller 79 (Step ST220).

The operator determines again whether or not the height position of the frame 18 and the positioning of the subject S are appropriate for imaging with reference to the scout image SI. In a case where the height position of the frame 18 and the positioning of the subject S are not appropriate for imaging, the operator turns on the irradiation field lamp 36 again and adjusts the height position of the frame 18 or performs the positioning of the subject S again.

In a case where the height position of the frame 18 and the positioning of the subject S are appropriate for imaging, as shown in FIG. 16, the operator inputs the main imaging instruction 100 through the input device 64. The main imaging instruction 100 is received in the reception unit 75 (in Step ST230, YES). With this, the main imaging command 101 is output from the imaging controller 77 to the radiation source 20 and the like (Step ST240).

As shown in FIG. 17, the rotation mechanism 50 is operated by the main imaging command 101, and the frame 18 is first rotated to the fourth rotation position (Step ST250). Thereafter, the frame 18 is rotated to the fifth rotation position at the first set rotation speed in the counterclockwise rotation direction CCW. In the interim, the subject S is irradiated with the radiation R for main imaging at each predetermined angle from the radiation tube 35, and the radiation detector 21 detects the radiation R transmitted through the subject S each time to obtain a plurality of projection images (Step ST260).

A plurality of projection images obtained in the radiation detector 21 are subjected to the reconstruction processing in the image processing unit 78 to generate the tomographic image TI. The tomographic image TI is displayed on the touch panel display 25 and the display 63 under the control of the display controller 79 (Step ST270).

The operator determines whether or not re-imaging of the tomographic image TI is required. In a case where the operator determines that re-imaging of the tomographic image TI is required (in Step ST280, YES), the operator re-inputs the main imaging instruction 100 through the input device 64, and the process returns to the processing of Step ST240.

In a case where the operator determines that re-imaging of the tomographic image TI is not required (in Step ST280, NO), as shown i FIG. 18, the operator inputs the return instruction 105 through the input device 64. The return instruction 105 is received in the reception unit 75 (in Step ST290, YES). With this, the return command 106 is output from the imaging controller 77 to the elevation mechanism 40 and the like (Step ST300).

The elevation mechanism 40 is operated by the return command 106 and the frame 18 is returned to the retreat height position. As shown in FIG. 19, the rotation mechanism 50 is operated and the frame 18 is returned from the fifth rotation position to the first rotation position at the second set rotation speed of a double speed of the first set rotation speed in the clockwise rotation direction CW (Step ST310). After the frame 18 is returned to the retreat height position, and the frame 18 is returned to the first rotation position, the operator retreats the subject S from the inside of the apparatus body 11 (Step ST320). A series of Steps ST100 to ST320 is repeatedly performed in a there is a next imaging order (in Step ST330, YES).

As described above, the CT apparatus 10 comprises the radiation source 20 that emits the radiation R, the radiation detector 21 that detects the radiation R, the annular frame 18 to which the radiation source 20 and the radiation detector 21 are attached and in which the subject S is positioned in the bore 19, and the three columns 14A to 14C that hold the frame 18 to be movable up and down in the vertical direction. For this reason, it is possible to make each column 14 thin compared to a case where the number of columns is two. Accordingly, it is possible to provide the CT apparatus 10 that allows the subject S to be easily visually recognized from the outside compared to a case where the number of columns is two, such that the columns are inevitably thick. The operator can easily perform the positioning of the subject S and can also easily perform the safety confirmation of the subject S during imaging. Furthermore, it is possible to reduce a floor occupation area of the apparatus body 11 compared to a case where the number of columns is two.

As shown in FIG. 4, in a case where the frame 18 is viewed in plan view and the triangle TA with the three columns 14A to 14C as the apexes is assumed, the center C of the frame 18 falls within the triangle TA.

On the contrary, a case where the center C of the frame 18 does not fall within the triangle TA is a case of a cantilever type in which, for example, the columns 14A and 14C are disposed on the back surface side with respect to the center C and no column is disposed on the front surface side with respect to the center C. In the case of the cantilever type, since weight balance significantly collapses, the installation stability of the frame 18 is degraded. Accordingly, in the embodiment, the three columns 14A to 14C are disposed such that the center C of the frame 18 falls within the triangle TA with the three columns 14A to 14C as the apexes. For this reason, it is possible to suppress degradation of the installation stability of the frame 18.

The frame 18 has an annular shape, and the columns 14A to 14C hold the frame 18 to be rotatable around the subject S. The rotating frame 18 is held by the three columns 14A to 14C, whereby it is possible to allow the subject S to be easily visually recognized from the outside and to maintain the rotation stability of the frame 18, compared to a case where the number of columns is two.

In the case of the cantilever type, the rotation stability of the frame 18 is also degraded. Then, degradation of the rotation stability of the frame 18 causes destabilization of a positional relationship between the radiation source 20 and the radiation detector 21 at each angle of main imaging. Accordingly, blur occurs in the projection image obtained at each angle, and as a result, the image quality of the tomographic image TI is deteriorated. In contrast, in the embodiment, as described above, since the three columns 14A to 14C are disposed such that the center C of the frame 18 falls within the triangle TA with the three columns 14A to 14C as the apexes, it is possible to dispel a concern that degradation of the rotation stability of the frame 18 causes deterioration of the image quality of the tomographic image TI.

As shown in FIG. 4, the three columns 14A to 14C are disposed at regular intervals on the same periphery. Since the weight of the frame 18 is applied to the three columns 14A to 14C with the best balance, it is possible to further increase the installation stability of the frame 18.

As shown in FIG. 1 and the like, the columns 14 have the openings 23 for allowing the subject S to be visually recognized from the outside. For this reason, it is possible to provide the CT apparatus 10 that allows the subject S to be more easily visually recognized from the outside.

Although an example where all the three columns 14A to 14C have the openings 23A to 23C has been described, the technique of the present disclosure is not limited thereto. For example, only one column 14 disposed beside the installation place of the control device 12 among the three columns 14A to 14C may have the opening 23. The opening is not limited to the rectangular opening 23 that extends in a longitudinal direction of the column 14 shown in the drawing. A plurality of circular openings or a mesh-patterned opening may be provided.

As shown in FIG. 1 and the like, the touch panel display 25 is attached to the column 14A through the movable arm 24. For this reason, the operator can input various instructions, such as the irradiation field confirmation instruction 90 or can view the scout image SI and the tomographic image TI in some cases at the installation place of the apparatus body 11, and it is possible to improve the convenience of the CT apparatus 10.

The technique of the present disclosure is not limited to the touch panel display 25 in which the input device and the display are combined, and at least one of the input device or the display may be attached to the column 14. The number of columns 14 to which at least one of the input device or the display is attached may be two or more.

As shown in FIG. 4, the column 14A provides the attachment portion 26 for the movable arm 24, and has rigidity higher than the columns 14B and 14C. For this reason, it is possible to restrain deformation of the column 14a due to the weight of the touch panel display 25, and to stably hold the touch panel display 25. The column 14A may be formed of a material having rigidity higher than the columns 14B and 14C.

As shown in FIG. 7, the CT apparatus 10 comprises the connecting member 17 that is connected to the frame 18 at the first connection position CP1 and is connected to the column 14 at the second connection position CP2. Then, the first connection position CP1 is higher than the second connection position CP2. For this reason, it is possible to perform imaging at the first connection position CP1 higher than the second connection position CP2.

The position of the highest point in the elevation range of the frame 18 can be higher than the first connection position CP1 by the height H as the difference between the first connection position CP1 and the second connection position CP2. As a result, it is possible to suppress the height of the column 14. Specifically, in a case where the position of the highest point in the elevation range of the frame 18 is 200 cm, and the height H is 30 cm, the height of the column 14 can be made about 170 cm. Then, it is possible to meet a height limit to the entrance or the like of the imaging room, and to perform movement between rooms using the caster 16 without hindrance. In moving the apparatus body 11 using the casters 16, the frame 18 is moved down from the position of the highest point in the elevation range.

As shown in FIG. 1 and the like, both the radiation source 20 and the radiation detector 21 protrude from the lower edge of the frame 18. For this reason, for example, it is possible to image a comparatively low imaging part, such as a waist of the subject S in a sitting posture, without significantly moving down the frame 18.

The apparatus body 11 comprises the casters 16 for transport. For this reason, it is possible to freely move the apparatus body 11. The installation place of the apparatus body 11 is not limited to the imaging room, and may be carried and installed in a patient's room or the like.

As shown in FIG. 6, the radiation source 20 emits the radiation R in a quadrangular pyramidal shape. For this reason, it is possible to finish imaging within a short time compared to a case where radiation R in a fan shape is scanned in a height direction from a radiation source and is detected in a radiation detector with pixels disposed in a one-dimensional manner. Instead of the quadrangular pyramidal shape, radiation R in a conical shape may be emitted.

As shown in FIGS. 1 and 5, the subject S is positioned in the bore 19 in any posture of the upright posture and the sitting posture. For this reason, it is possible to meet demands of a physician who wants to observe a soft tissue, such as a lung, in a natural state with gravity or wants to observe a joint, such as a hip joint, in a state in which a load is applied with gravity.

Figure 2:
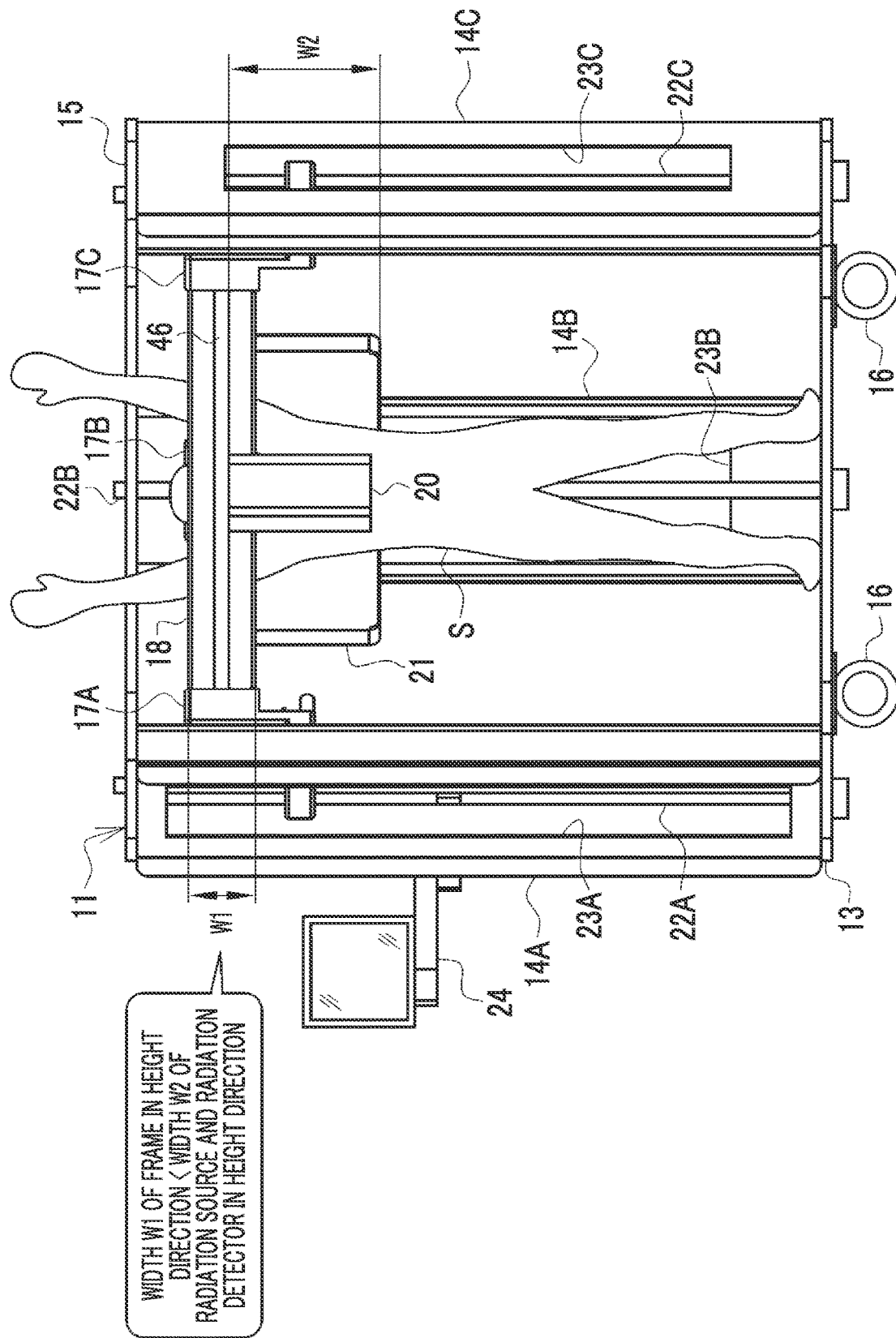
FIG. 2 is a front view of an apparatus body of the CT apparatus.
Figure 3:
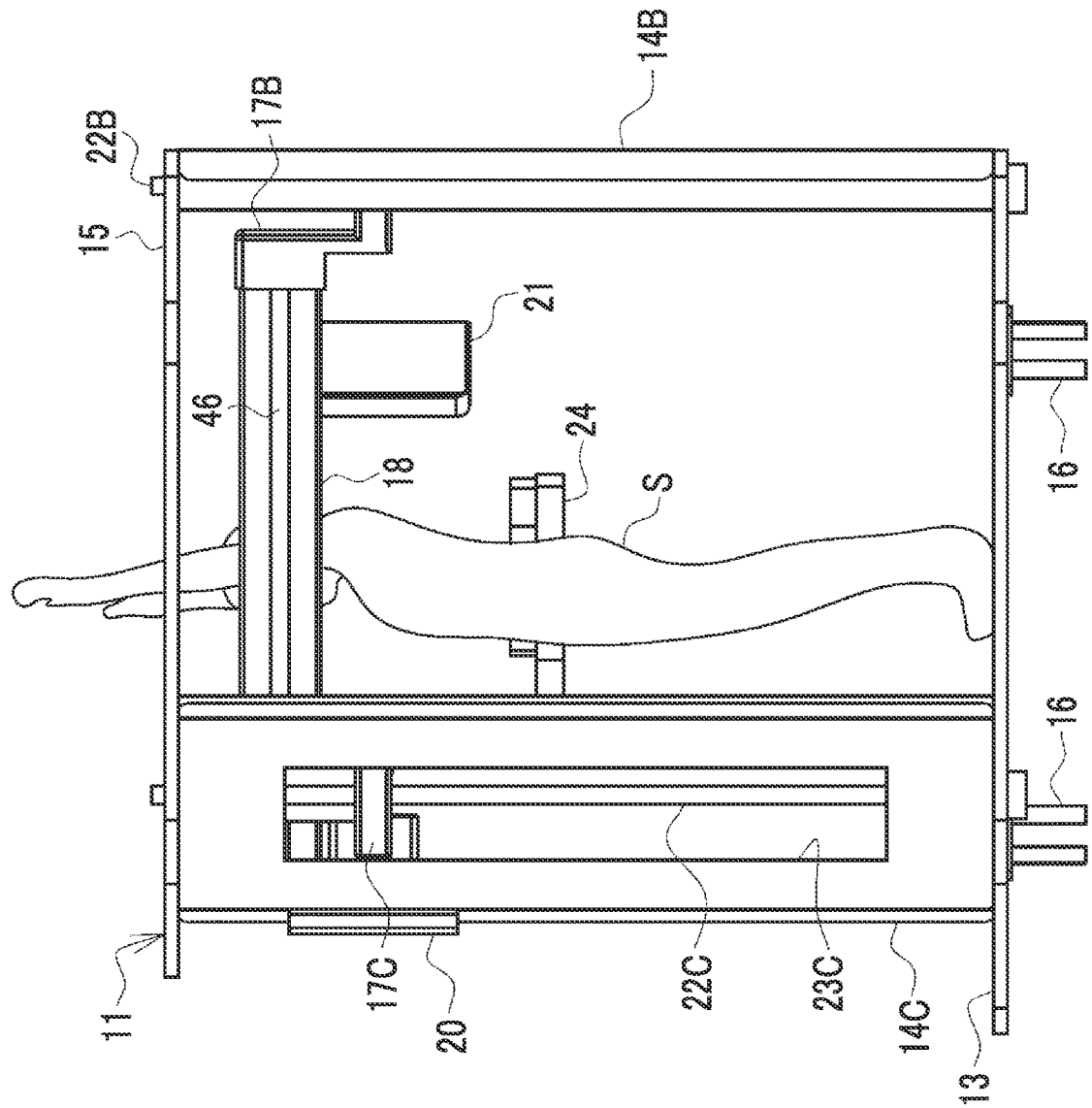
FIG. 3 is a side view of the apparatus body of the CT apparatus.

The CT apparatus 10 comprises the radiation source 20 that emits the radiation R, the radiation detector 21 that detects the radiation R, the annular frame 18 that rotates around the subject S positioned in the bore 19, the three columns 14 that holds the frame 18 to be rotatable and movable up and down in the vertical direction, the elevation mechanism 40 that moves up and down the frame 18, and the rotation mechanism 50 that rotates the frame 18. The radiation source 20 and the radiation detector 21 are attached to the frame 18 at positions facing each other. As shown in FIG. 2, the frame 18 has the width W1 smaller than the width W2 of the radiation source 20 and the radiation detector 21 in the height direction over the whole periphery. As shown in FIG. 18, the imaging controller 77 performs control for operating the elevation mechanism 40 in response to the return instruction 105 from the operator to move the frame 18 to the retreat height position set at the position of the highest point in the elevation range of the frame 18 on the upper end side of the columns 14. The imaging controller 77 performs control for operating the rotation mechanism 50 in response to the return instruction 105 from the operator to rotate the frame 18 to the position of 60° as the first rotation position where the radiation source 20 overlaps the column 14A.

Since the frame 18 is rotated to the first rotation position where the radiation source 20 overlaps the column 14A, as shown in FIG. 11, when the subject S approaches inside the apparatus body 11 from between the columns 14A and 14C, the radiation source 20 does not obstruct subject S. For this reason, there is no need to move up the frame 18 to a position where the radiation source 20 exceeds the head of the subject S. Accordingly, unlike the related art, there is no need to secure a comparatively large retreat space for retreating the frame 18 over the head of the subject S in an upper portion of the apparatus body 11. That is, it is possible to make the apparatus body 11 compact in the height direction compared to the related art.

As shown in FIG. 14, the imaging controller 77 performs control for operating the rotation mechanism 50 in response to the scout imaging instruction 95 from the operator to move the frame 18 to the scout imaging position for scout imaging before main imaging. The scout imaging position is at least one of the second rotation position where the radiation source 20 confronts the subject S or the third rotation position where the radiation source 20 faces the side surface of the subject S. For this reason, it is possible to simply perform scout imaging without troubling the operator so much.

As shown in FIGS. 16 and 17, the imaging controller 77 operates the rotation mechanism 50 to rotate the frame 18 to the fourth rotation position, and then, causes the radiation source 20 and the radiation detector 21 to perform main imaging while rotating the frame 18 to the fifth rotation position. For this reason, it is possible to simply perform main imaging without troubling the operator so much.

As shown in FIGS. 18 and 19, the imaging controller 77 operates the rotation mechanism 50 to return the frame 18 from the fifth rotation position to the first rotation position after main imaging. For this reason, it is possible to simply return the frame 18 to the first rotation position without troubling the operator so much.

In returning the frame 18 from the fifth rotation position to the first rotation position, the imaging controller 77 rotates the frame 18 in a direction (in the example, the from the clockwise rotation direction CW) from the fifth rotation position toward the fourth rotation position. The direction from the fifth rotation position toward the fourth rotation position is opposite to a rotation direction (in the example, the counterclockwise rotation direction CCW) of the frame 18 in main imaging. For this reason, the radiation source 20 and the radiation detector 21 follows a trajectory of movement in main imaging without hitting against the subject S. Accordingly, in a case where the subject S keeps still, there is no concern that the radiation source 20 and the radiation detector 21 hit against the subject S, and it is possible to secure the safety of the subject S.

In returning the frame 18 from the fifth rotation position to the first rotation position, the imaging controller 77 rotates the frame 18 at the second set rotation speed, specifically, the double speed higher than the first set rotation speed from the fourth rotation position to the fifth rotation position. For this reason, it is possible to finish work for returning the frame 18 from the fifth rotation position to the first rotation position within a short time, and to reduce the stress of the subject S who is waiting inside the apparatus body 11.

Figure 23:
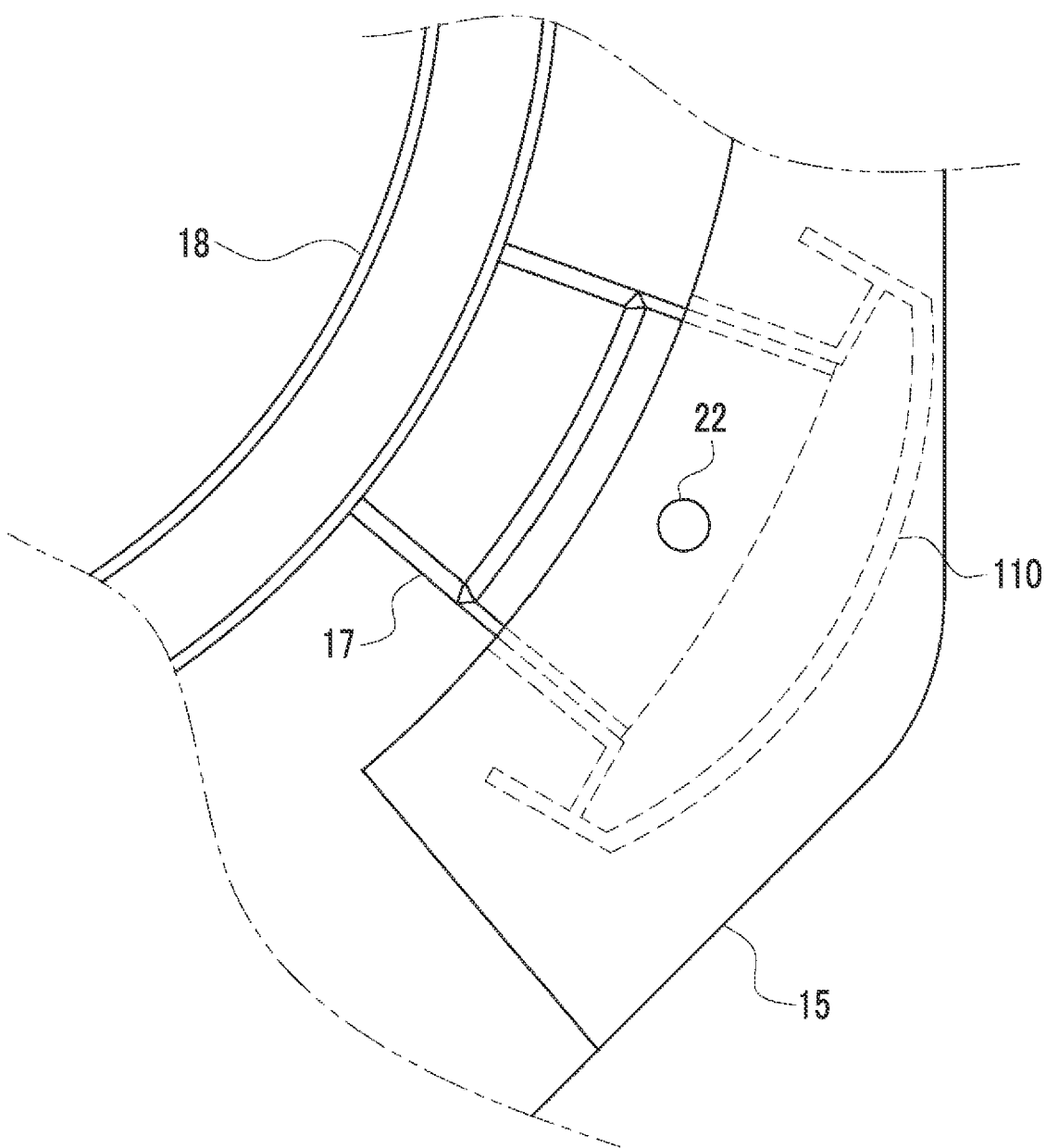
FIG. 23 is a diagram showing another example of columns.

The columns are not limited to the straight shape shown in the drawing. As a column 110 shown in FIG. 23 as an example, in a case where the frame 18 is viewed from a direction in plan view, the column may have an arc shape following the frame 18. With such a shape, it is possible to further increase the strength of the column 110.

Figure 24:
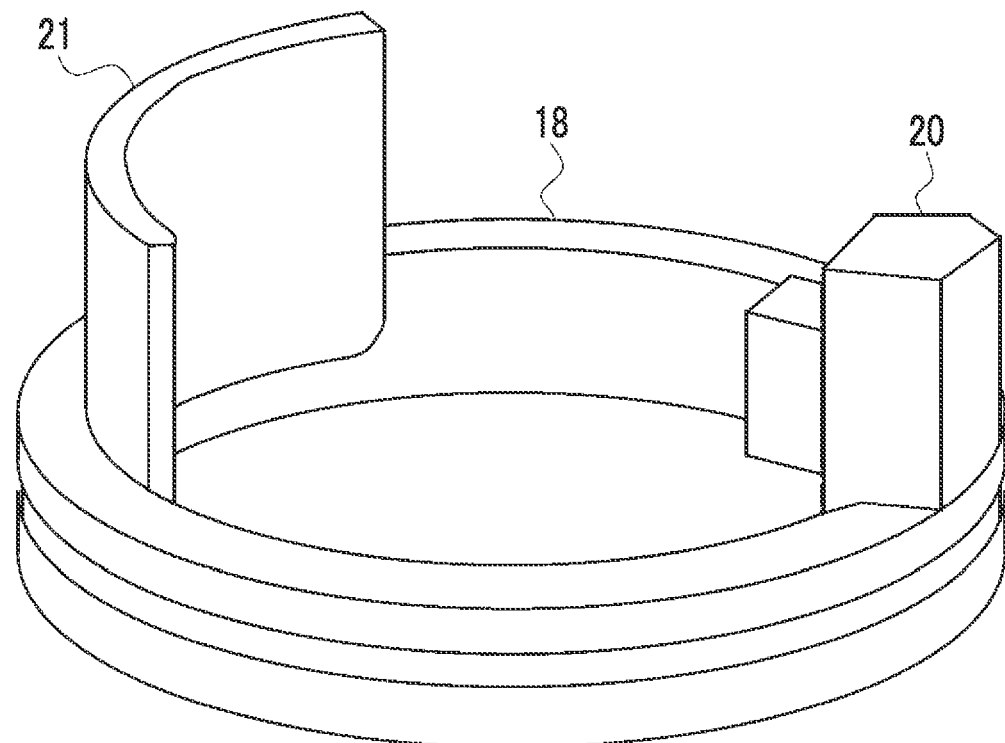
FIG. 24 is a diagram showing an aspect where the radiation source and the radiation detector protrude from an upper edge of the frame.

Although an aspect where both the radiation source 20 and the radiation detector 21 protrude from the lower edge of the frame 18 has been shown, the technique of the present disclosure is not limited thereto. As shown in FIG. 24 as an example, an aspect where both the radiation source 20 and the radiation detector 21 protrude from an upper edge of the frame 18 may be made. Then, for example, it is possible to image a comparatively high imaging part, such as a head of the subject S in an upright posture, without significantly moving up the frame 18.

Figure 25:
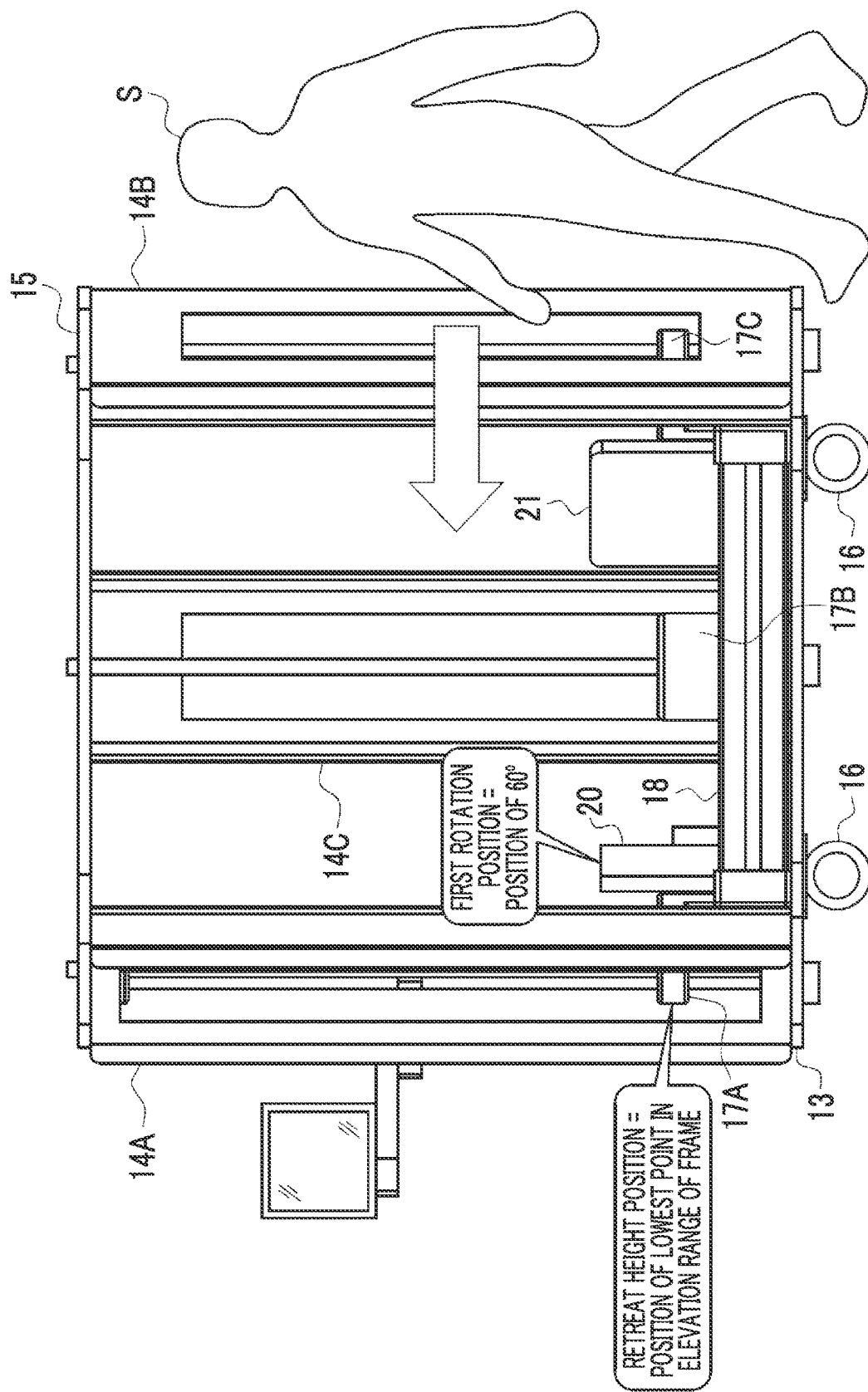
FIG. 25 is a diagram showing the retreat height position and the first rotation position in the aspect shown in FIG. 24.

In an aspect shown in FIG. 24, the retreat height position is set to a position shown in FIG. 25 as an example. In FIG. 25, the retreat height position is set on a lower end side of the column 14. In more detail, the retreat height position is a position of a lowest point in the elevation range of the frame 18. As described above, the position of the lowest point in the elevation range of the frame 18 is a position of a substantially lower end of the column 14 and is a position where the first connecting part 43 is in contact with the front surface of the stage 13. In contrast with an aspect where both the radiation source 20 and the radiation detector 21 protrude from the lower edge of the frame 18, in the connecting member 17, the first connecting part 43 is disposed downside, and the second connecting part 44 is disposed upside. In this case, the subject S approaches inside the apparatus body 11 across the frame 18. Similarly to the arrow shown in FIG. 11, an arrow shown in FIG. 25 indicates a direction in which the subject S is led inside the apparatus body 11.

As described above, the width W1 of the frame 18 in the height direction is smaller than the width W2 of the radiation source 20 and the radiation detector 21 in the height direction. For this reason, a burden on the subject S is reduced compared to the related art in which an imaging unit having the same width as the radiation source 20 and the radiation detector 21 is placed over the subject. Accordingly, it is possible to allow the subject S to easily approach inside the apparatus body 11 compared to the related art.

Although the position of 60° where the radiation source 20 overlaps the column 14A has been shown as the first rotation position, the technique of the present disclosure is not limited thereto. A position of 300° where the radiation source 20 overlaps the column 14C may be set as the first rotation position. Alternatively, a position of 180° where the radiation source 20 overlaps the column 14B may be set as the first rotation position, and the subject S may be allowed to approach inside the apparatus body 11 from between the columns 14B and 14C.

Figure 26:
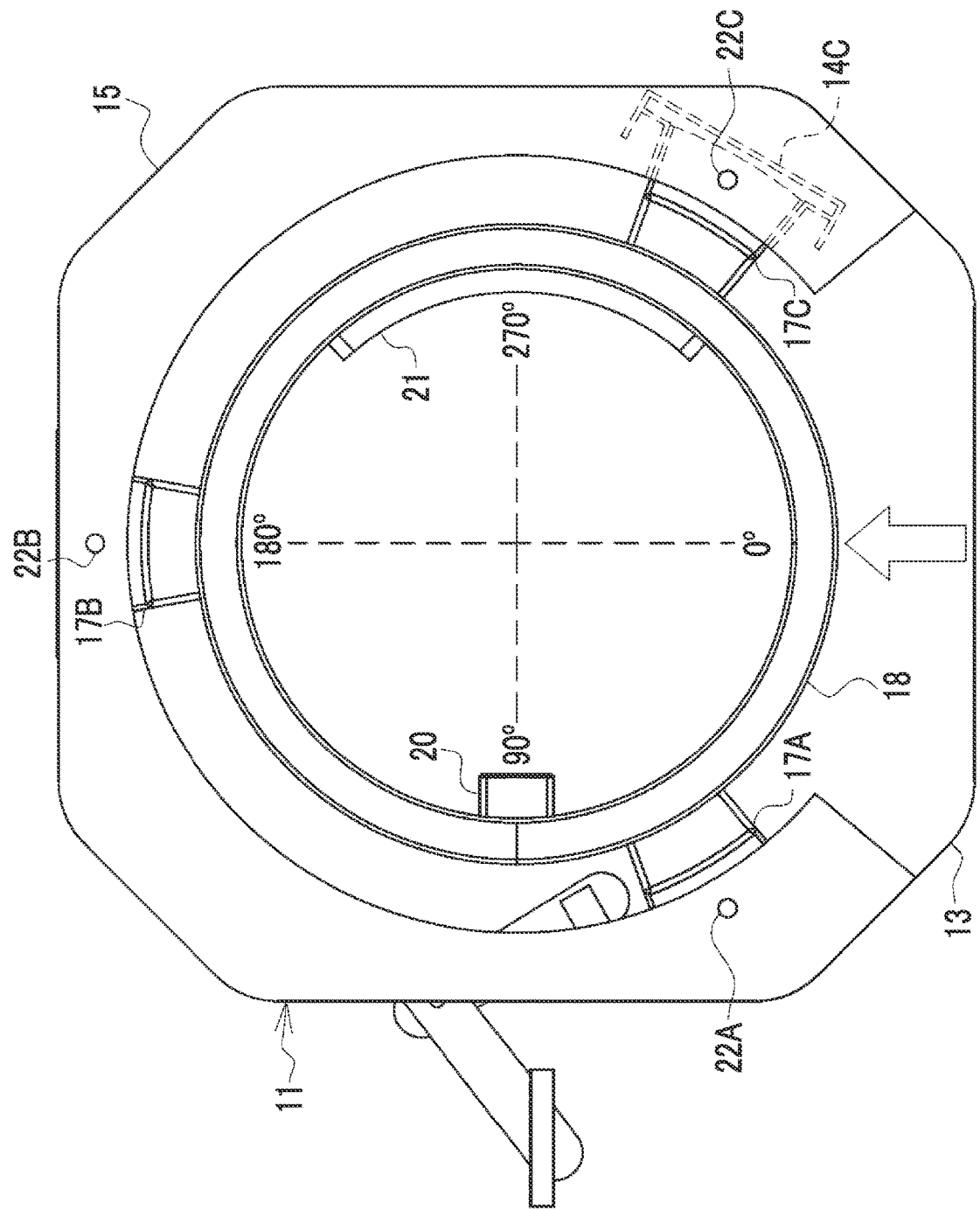
FIG. 26 is a diagram showing another example of the first rotation position.

A unit that overlaps the column 14 at the first rotation position is not limited to the radiation source 20. The radiation detector 21 may overlap the column 14 at the first rotation position. A portion that overlaps the column 14 is not limited to the whole of the radiation source 20 or the radiation detector 21, and at least one of at least a part of the radiation source 20 or at least a part of the radiation detector 21 may overlap the column 14. For example, as shown in FIG. 26, a position of 90° where a right end portion of the radiation detector 21 overlaps the column 14C may be set as the first rotation position. Similarly to the arrow shown in FIG. 12, an arrow shown in FIG. 26 indicates a direction in which the subject S is let inside the apparatus body 11.

Figure 27:
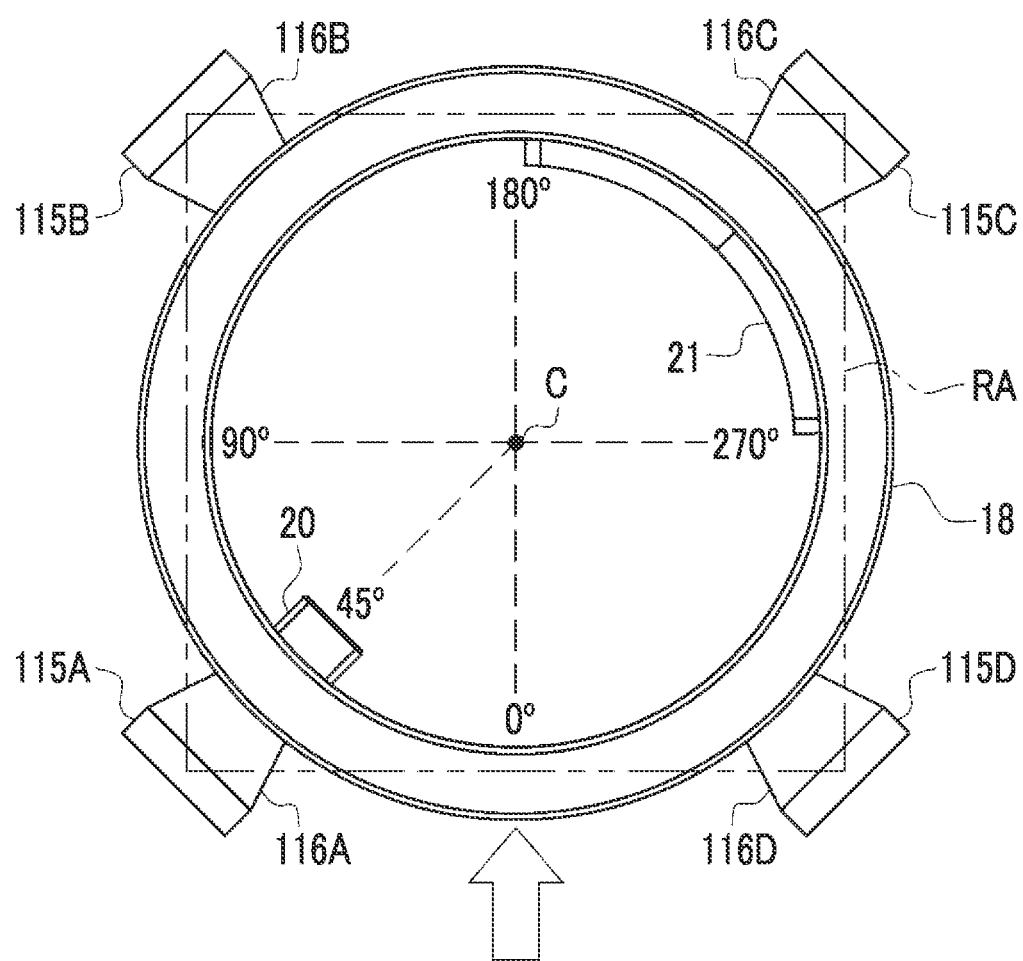
FIG. 27 is a diagram showing an example of four columns.

The numbers of columns is not limited to three. As shown in FIG. 27 as an example, four columns 115A, 115B, 115C, and 115D may be disposed at positions of 45°, 135°, 225°, and 315°. Even in this case, the center C of the frame 18 falls within a quadrangle RA with the four columns 115A to 115D as apexes. The column 115A is connected to the frame 18 through a connecting member 116A, and the column 115B is connected to the frame 18 through a connecting member 116B. The column 115C is connected to the frame 18 through a connecting member 116C, and the column 115D is connected to the frame 18 through a connecting member 116D. In this case, for example, a position of 45° where the radiation source 20 overlaps the column 115A is set as the first rotation position, and the subject S is allowed to approach inside the apparatus body 11 from between the columns 115A and 115D.

Figure 28:
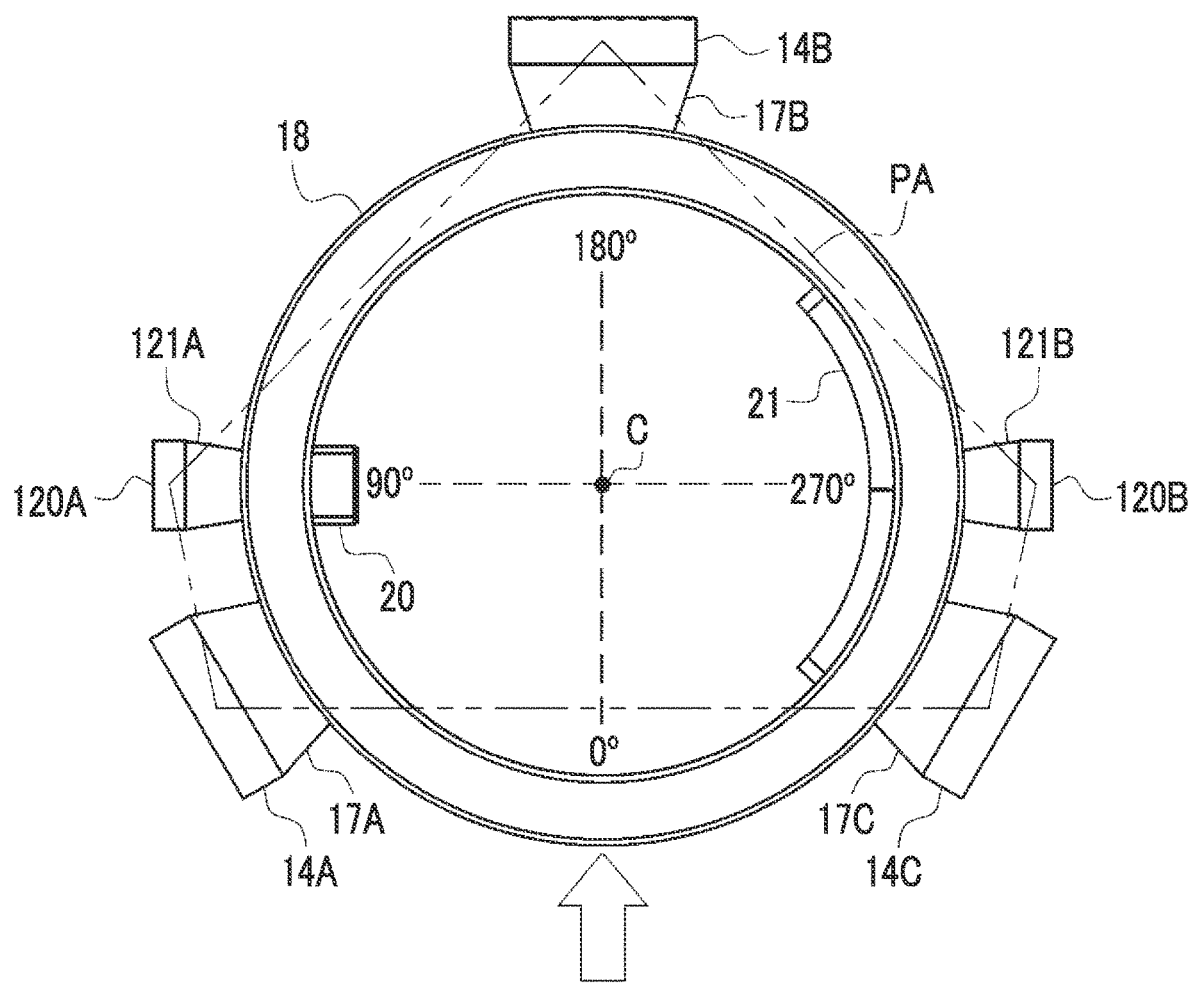
FIG. 28 is a diagram showing an example of five columns.

As shown in FIG. 28 as an example, columns 120A and 120B for reinforcement may be disposed at a position of 90° backward of the column 14A and a position of 270° backward of the column 14C. Even in this case, the center C of the frame 18 falls within a pentagon PA with the five columns 14A to 14C, 120A, and 120B as apexes. The column 120A is connected to the frame 18 through a connecting member 121A, and the column 120B is connected to the frame 18 through a connecting member 121B. In this case, for example, a position of 90° where the radiation source 20 overlaps the column 120A, the right end portion of the radiation detector 21 overlaps the column 14C, and a central portion of the radiation detector 21 overlaps the column 120B is set as the first rotation position, and the subject S is allowed to approach inside the apparatus body 11 from between the columns 14A and 14C.

Figure 29:
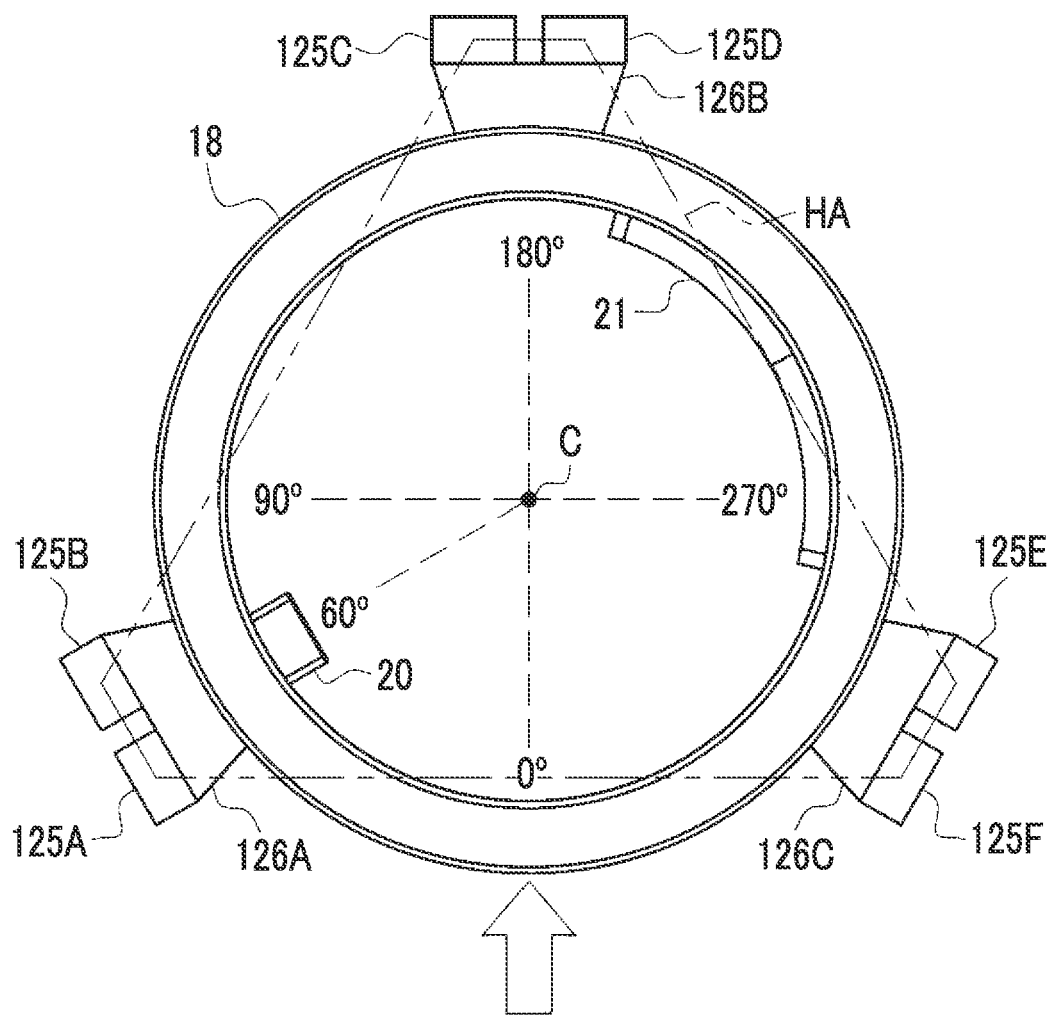
FIG. 29 is a diagram showing an example of six columns.

As shown in FIG. 29 as an example, a pair of columns 125A and 125B may be disposed at a position of 60°, a pair of columns 125C and 125D may be disposed at a position of 180°, and a pair of columns 125E and 125F may be disposed at a position of 300°. Even in this case, the center C of the frame 18 falls within a hexagon HA with the six columns 125A to 125F as apexes. The columns 125A and 125B have a size substantially half of the column 14A, the columns 125C and 125D have a size substantially half of the column 14B, and the columns 125E and 125F have a size substantially half of the column 14C. The columns 125A and 125B are connected to the frame 18 through a connecting member 126A, the columns 125C and 125D are connected to the frame 18 through a connecting member 126B, and the columns 125E and 125F are connected to the frame 18 through a connecting member 126C. In this case, for example, a position of 60° where the radiation source 20 overlaps the columns 125A and 125B is set as the first rotation position, and the subject S is allowed to approach inside the apparatus body 11 from between the columns 125A and 125F. As will be understood from the examples of FIGS. 28 and 29, the arrangement of the columns may not be at regular intervals.

Figure 30:
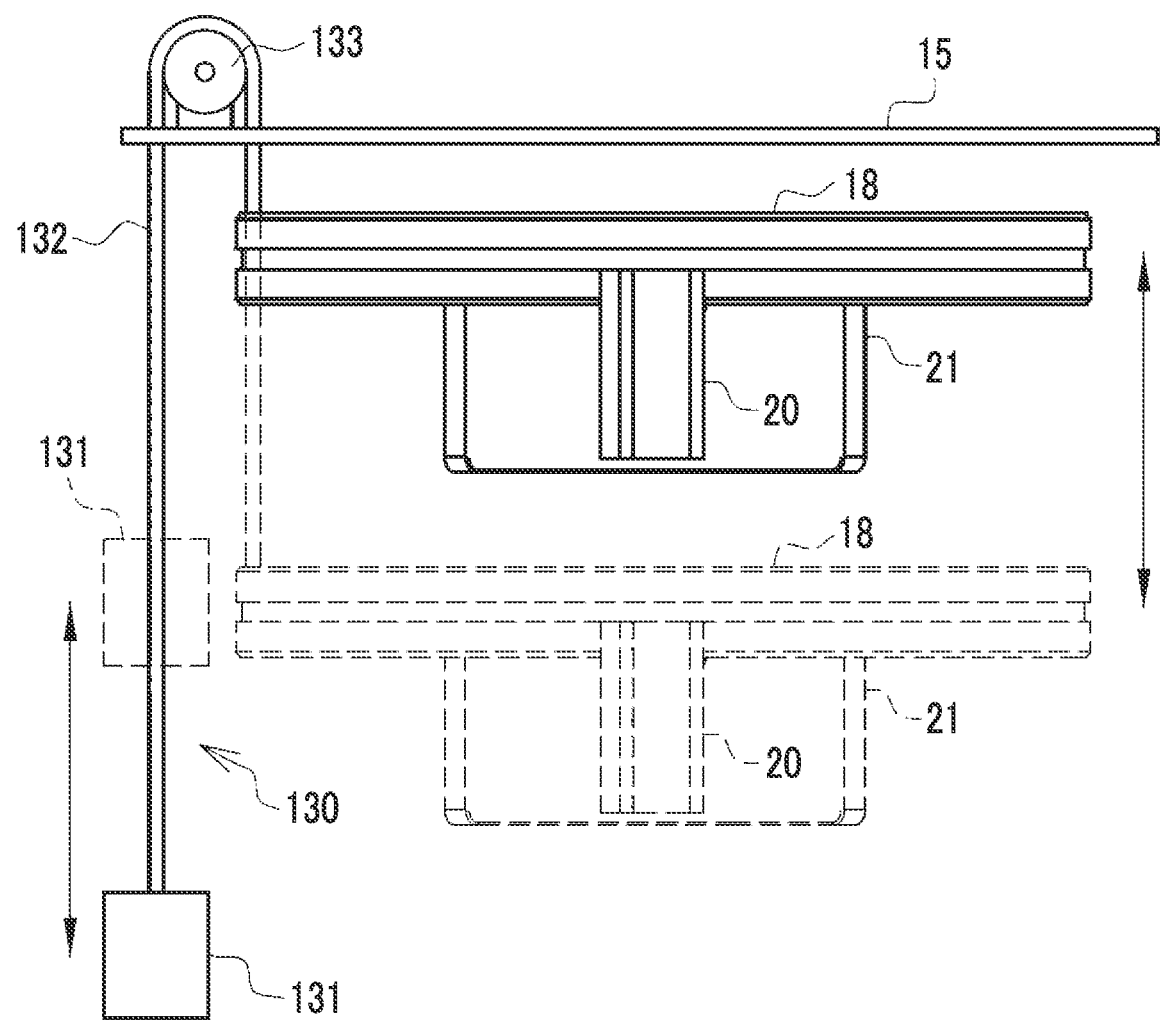
FIG. 30 is a diagram showing an elevation mechanism using a counterweight.

The elevation mechanism of the frame 18 is not limited to the ball screw mechanism shown in the drawing. An elevation mechanism 130 shown in FIG. 30 as an example may be employed. In FIG. 30, the elevation mechanism 130 is configured of a counterweight 131, a wire 132, and a pulley 133. The counterweight 131 has a weight required for balancing with the frame 18 to which the radiation source 20 and the radiation detector 21 are attached. One end of the wire 132 is attached to the counterweight 131. The wire 132 is inserted into the top plate 15 and is wound on the pulley 133 provided on the front surface of the top plate 15. The wire 132 is inserted into the top plate 15 again, and the other end thereof is attached to the frame 18. The frame 18 is moved up and down depending on an operator's manual operation to move up and down.

In this way, in a case where the elevation mechanism 130 using the counterweight 131 is used, the operator can set the position of the frame 18 depending on a sense of the hand of the operator. Both the elevation mechanism 40 of the ball screw mechanism and the elevation mechanism 130 using the counterweight 131 may be mounted in the apparatus body 11, and the elevation mechanism 40 and the elevation mechanism 130 may be switched by a clutch or the like.

The motor 52 for rotation may be configured of a stepping motor, and a rotation position of the frame 18 may be derived depending on the number of pulses applied to the motor 52 for rotation. The number of columns may be two.

Although the CT apparatus 10 has been shown as the medical image capturing apparatus, the technique of the present disclosure is not limited thereto. A simple radiography apparatus that captures a projection image while changing an angle one by one may be employed. A radiography apparatus that has a frame, to which two sets of radiation source 20 and radiation detector 21 are attached, irradiates the subject S with the radiation R simultaneously from the front surface and the side surface of the subject S to obtain two projection images, and checks anatomical shapes of a hip joint and a spine of the subject S and a connection condition of a spine and a lower limb.

The hardware configuration of the computer configuring the control device 12 can be modified in various ways. For example, the control device 12 may be configured of a plurality of computers separated as hardware for the purpose of improving processing ability and reliability. For example, the functions of the reception unit 75 and the RW controller 76 and the functions of the imaging controller 77, the image processing unit 78, and the display controller 79 may be distributed to two computers. In this case, the control device 12 is configured of two computers.

In this way, the hardware configuration of the computer of the control device 12 can be appropriately changed depending on required performance, such as processing ability, safety, or reliability. Not only hardware but also an application program, such as the operation program 70, can be of course duplicated or distributed and stored in a plurality of storages for the purpose of securing safety and reliability.

In the above-described embodiment, for example, as the hardware structures of processing units that execute various kinds of processing, such as the reception unit 75, the RW controller 76, the imaging controller 77, the image processing unit 78, and the display controller 79, various processors described below can be used. Various processors include a programmable logic device (PLD) that is a processor capable of changing a circuit configuration after manufacture, such as a field programmable gate array (FPGA), and/or a dedicated electric circuit that is a processor having a circuit configuration dedicatedly designed for executing specific processing, such as an application specific integrated circuit (ASIC), in addition to the CPU 62 that is a general-purpose processor configured to execute software (operation program 70) to function as various processing units.

One processing unit may be configured of one of various processors described above or may be configured of a combination of two or more processors (for example, a combination of a plurality of FPGAs and/or a combination of a CPU and an FPGA) of the same type or different types. A plurality of processing units may be configured of one processor.

As an example where a plurality of processing units are configured of one processor, first, as represented by a computer, such as a client or a server, there is a form in which one processor is configured of a combination of one or more CPUs and software and the processor functions as a plurality of processing units. Secondly, as represented by system on chip (SoC) or the like, there is a form in which a processor that realizes all functions of a system including a plurality of processing units into one integrated circuit (IC) chip is used. In this way, various processing units may be configured using one or more processors among various processors described above as a hardware structure.

In addition, as the hardware structure of various processors, more specifically, an electric circuit (circuitry), in which circuit elements, such as semiconductor elements, are combined, can be used.

The technique of the present disclosure can also be appropriately combined with various embodiments and/or various modification examples described above. The technique of the present disclosure is not limited to the above-described embodiments, and various configurations can be of course employed without departing from the spirit and scope of the technique of the present disclosure. In addition to the program, the technique of the present disclosure extends to a storage medium that stores the program in a non-transitory manner.

The content of the above description and the content of the drawings are detailed description of portions according to the technique of the present disclosure, and are merely examples of the technique of the present disclosure. For example, the above description relating to configuration, function, operation, and advantageous effects is description relating to configuration, function, operation, and advantageous effects of the portions according to the technique of the present disclosure. Thus, it is needless to say that unnecessary portions may be deleted, new elements may be added, or replacement may be made to the content of the above description and the content of the drawings without departing from the gist of the technique of the present disclosure. Furthermore, to avoid confusion and to facilitate understanding of the portions according to the technique of the present disclosure, description relating to common technical knowledge and the like that does not require particular description to enable implementation of the technique of the present disclosure is omitted from the content of the above description and the content of the drawings.

In the specification, "A and/or B" is synonymous with "at least one of A or B". That is, "A and/or B" may refer to A alone, B alone, or a combination of A and B. Furthermore, in the specification, a similar concept to "A and/or B" applies to a case in which three or more matters are expressed by linking the matters with "and/or".

All cited documents, patent applications, and technical standards described in the specification are incorporated by reference in the specification to the same extent as in a case where each individual cited document, patent application, or technical standard is specifically and individually indicated to be incorporated by reference.

What is claimed is:

1. A medical image capturing apparatus comprising:
an x-ray radiation source that emits x-ray radiation;
an x-ray radiation detector that detects the x-ray radiation;
an annular frame to which the x-ray radiation source and the x-ray radiation detector are attached at positions facing each other and that rotates around a subject positioned in a bore, the frame having a width smaller than a width of the x-ray radiation source and the x-ray radiation detector in a height direction over a whole periphery, and both the x-ray radiation source and the x-ray radiation detector protruding from either an upper edge or a lower edge;
a plurality of columns that hold the frame to be rotatable and movable up and down in a vertical direction;
a moving mechanism that moves up and down and rotates the frame;
a processor; and
a memory connected to or embedded in the processor, wherein the processor
performs control for operating the moving mechanism to move the frame to a retreat height position set on an upper end side or a lower end side of the columns and control for operating the moving mechanism to rotate the frame to a first rotation position where at least one of at least a part of the x-ray radiation source or at least a part of the x-ray radiation detector overlaps the columns, in response to an operation instruction from an operator.

2. The medical image capturing apparatus according to claim 1,
wherein the x-ray radiation source and the x-ray radiation detector protrude from the lower edge, and
the retreat height position is a position of a highest point in an elevation range of the frame.

3. The medical image capturing apparatus according to claim 1,
wherein the x-ray radiation source and the x-ray radiation detector protrude from the upper edge, and
the retreat height position is a position of a lowest point in an elevation range of the frame.

4. The medical image capturing apparatus according to claim 1,
wherein the processor performs control for operating the moving mechanism to move the frame to a scout imaging position where scout imaging is performed before main imaging and that is at least one of a second rotation position where the x-ray radiation source confronts the subject or a third rotation position where the x-ray radiation source faces a side surface of the subject, in response to the operation instruction from the operator.

5. The medical image capturing apparatus according to claim 4,
wherein the processor operates the moving mechanism to rotate the frame to a fourth rotation position, and then, causes the x-ray radiation source and the x-ray radiation detector to perform main imaging while rotating the frame to a fifth rotation position.

6. The medical image capturing apparatus according to claim 5,
wherein the processor operates the moving mechanism after the main imaging to return the frame from the fifth rotation position to the first rotation position.

7. The medical image capturing apparatus according to claim 6,
wherein the processor rotates the frame in a direction from the fifth rotation position toward the fourth rotation position in a case of returning the frame from the fifth rotation position to the first rotation position.

8. The medical image capturing apparatus according to claim 6,
wherein the processor rotates the frame at a rotation speed higher than a rotation speed from the fourth rotation position to the fifth rotation position in a case of returning the frame from the fifth rotation position to the first rotation position.

9. The medical image capturing apparatus according to claim 1, further comprising:
casters for transport.

10. The medical image capturing apparatus according to claim 1,
wherein the x-ray radiation source emits the x-ray radiation having a pyramidal shape.

11. The medical image capturing apparatus according to claim 1, wherein the subject is positioned in the bore in any one of an upright posture or a sitting posture.

12. An operation method of a medical image capturing apparatus including an x-ray radiation source that emits x-ray radiation, an x-ray radiation detector that detects the x-ray radiation, an annular frame to which the x-ray radiation source and the x-ray radiation detector are attached at positions facing each other and that rotates around a subject positioned in a bore, the frame having a width smaller than a width of the x-ray radiation source and the x-ray radiation detector in a height direction over a whole periphery, and both the x-ray radiation source and the x-ray radiation detector protruding from either an upper edge or a lower edge, a plurality of columns that hold the frame to be rotatable and movable up and down in a vertical direction, and a moving mechanism that moves up and down and rotates the frame, the operation method comprising:

performing control for operating the moving mechanism to move the frame to a retreat height position set on an upper end side or a lower end side of the columns and control for operating the moving mechanism to rotate the frame to a first rotation position where at least one of at least a part of the x-ray radiation source or at least a part of the x-ray radiation detector overlaps the columns, in response to an operation instruction from an operator.

13. A non-transitory computer-readable storage medium storing an operation program for a medical image capturing apparatus including an x-ray radiation source that emits x-ray radiation, an x-ray radiation detector that detects the x-ray radiation, an annular frame to which the x-ray radiation source and the x-ray radiation detector are attached at positions facing each other and that rotates around a subject positioned in a bore, the frame having a width smaller than a width of the x-ray radiation source and the x-ray radiation detector in a height direction over a whole periphery, and both the x-ray radiation source and the x-ray radiation detector protruding from either an upper edge or a lower edge, a plurality of columns that hold the frame to be rotatable and movable up and down in a vertical direction, and a moving mechanism that moves up and down and rotates the frame, the operation program causing a computer to execute a process comprising:

performing control for operating the moving mechanism to move the frame to a retreat height position set on an upper end side or a lower end side of the columns and control for operating the moving mechanism to rotate the frame to a first rotation position where at least one of at least a part of the x-ray radiation source or at least a part of the x-ray radiation detector overlaps the columns, in response to an operation instruction from an operator.

* * * * *